(12) United States Patent
Baudel et al.

(10) Patent No.: US 9,976,195 B2
(45) Date of Patent: May 22, 2018

(54) METHOD FOR PROCESSING VEGETABLE BIOMASS

(75) Inventors: Henrique Macedo Baudel, Piracicaba (BR); Jose Augusto Travassos Rios Tome, Piracicaba (BR); Dionisio Fabiano Pegoretti, Piracicaba (BR); Dionisio Morelli Filho, Americana (BR); Oswaldo Godoy Neto, Piracicaba (BR); Jaime Fingerut, Piracicaba (BR); Celia Maria Araujo Galvao, Americana (BR); Liliane Pires Andrade, Piracicaba (BR)

(73) Assignee: CTC—Centro de Tecnologia Canavieira—S.A., Piracicaba (BR)

( * ) Notice: Subject to any disclaimer, the term of this patent is extended or adjusted under 35 U.S.C. 154(b) by 516 days.

(21) Appl. No.: 13/512,615

(22) PCT Filed: Nov. 30, 2010
(Under 37 CFR 1.47)

(86) PCT No.: PCT/BR2010/000397
§ 371 (c)(1),
(2), (4) Date: Jun. 30, 2013

(87) PCT Pub. No.: WO2011/063484
PCT Pub. Date: Jun. 3, 2011

(65) Prior Publication Data
US 2014/0053827 A1    Feb. 27, 2014

(30) Foreign Application Priority Data
Nov. 30, 2009 (BR) ..................... 0904538

(51) Int. Cl.
| | |
|---|---|
| *C13K 13/00* | (2006.01) |
| *C12P 7/10* | (2006.01) |
| *C13B 5/04* | (2011.01) |
| *C13K 1/02* | (2006.01) |
| *C08H 8/00* | (2010.01) |
| *C13B 10/02* | (2011.01) |
| *C13B 35/00* | (2011.01) |
| *C10L 1/02* | (2006.01) |
| *C12P 19/02* | (2006.01) |
| *A23K 10/12* | (2016.01) |
| *A23K 10/37* | (2016.01) |

(52) U.S. Cl.
CPC ............ *C13K 13/007* (2013.01); *A23K 10/12* (2016.05); *A23K 10/37* (2016.05); *C08H 8/00* (2013.01); *C10L 1/023* (2013.01); *C12P 7/10* (2013.01); *C12P 19/02* (2013.01); *C13B 5/04* (2013.01); *C13B 10/02* (2013.01); *C13B 35/00* (2013.01); *C13K 1/02* (2013.01); *C13K 13/002* (2013.01); *C10G 2300/1014* (2013.01); *C12P 2201/00* (2013.01); *Y02E 50/16* (2013.01); *Y02E 50/17* (2013.01); *Y02P 30/20* (2015.11); *Y02P 60/877* (2015.11)

(58) Field of Classification Search
CPC .......... C13K 13/007; C13B 10/02; C13B 5/04
See application file for complete search history.

(56) References Cited

U.S. PATENT DOCUMENTS

| | | |
|---|---|---|
| 4,326,063 A | 4/1982 | Son |
| 4,356,196 A | 10/1982 | Hultquist |
| 5,037,663 A | 8/1991 | Dale |
| 5,266,120 A | 11/1993 | Dambrine |
| 5,705,369 A * | 1/1998 | Torget et al. ............. 435/105 |
| 5,772,775 A | 6/1998 | Riviere |
| 6,416,621 B1 | 7/2002 | Karstens |
| 7,189,306 B2 | 3/2007 | Gervais |
| 2007/0031918 A1 | 2/2007 | Dunson, Jr. |
| 2007/0031919 A1 | 2/2007 | Dunson, Jr. |
| 2008/0008783 A1 | 1/2008 | Dale |
| 2008/0045762 A1* | 2/2008 | Foody et al. .............. 585/240 |
| 2010/0152435 A1* | 6/2010 | Stapley ................. C07B 41/08 536/123.12 |
| 2011/0065785 A1* | 3/2011 | Larsen ..................... C12P 7/06 514/461 |

(Continued)

FOREIGN PATENT DOCUMENTS

WO    WO 2009/124370    * 10/2009

OTHER PUBLICATIONS

Interpretation of deacetylation and hemicellulose hydrolysis during hydrothermal treatments on the basis of the severity factor Gil Garrote et al. Process Biochemistry vol. 37, pp. 1067-1073, 2002.*
Features of promising technologies for pretreatment of lignocellulosic biomass Nathan Mosier et al. Bioresource Technology vol. 96, pp. 673-686, 2005*
Pretreatment of Lignocellulosic Materials for Efficient Bioethanol Production BioFuels, vol. 108, pp. 41-65, 2007 M. Galbe et al.*

(Continued)

*Primary Examiner* — Douglas B Call
(74) *Attorney, Agent, or Firm* — Laurence P. Colton; Smith Tempel Blaha LLC

(57) ABSTRACT

The present invention relates to an energy-efficient process for the treatment of plant biomass, particularly sugar cane, for the production of carbohydrates and ethanol, using physico-chemical and extraction techniques, as well as very simple milling configurations, thereby minimizing energy consumption during extraction of the cane juice.

The biomass treated and obtained through this process, when subjected to a fermentation process for the production of ethanol, increases the yield of the process in comparison with that of traditional sugar cane. It can also be used for the production of enzymes, animal feedstuffs, and other useful products.

9 Claims, 18 Drawing Sheets

(56) References Cited

U.S. PATENT DOCUMENTS

2011/0097777 A1* 4/2011 Oliveira .................. C13B 5/02
435/161
2011/0300586 A1* 12/2011 Liu ........................ C08H 8/00
435/99

OTHER PUBLICATIONS

Analysis of Sugar Cane Saccharides by Liquid Chromatography. 2. Ion-Exchange Resins J. Wong-Chong and F. A. Martin J. Agric. Food Chem., vol. 27, No. 5, pp. 929-932, 1979.*

Composition of sugar cane, energy cane, and sweet sorghum suitalbe for ethanol production at Louisiana sugar mills Misook Kim et al. J. Ind. Microbiol. Biotechnol. vol. 38, pp. 803-807, 2011, published online Aug. 29, 2010.*

* cited by examiner

METHOD FOR PROCESSING VEGETABLE BIOMASS

FIELD OF THE INVENTION

The present invention relates to an energy-efficient process for the treatment of plant biomass, particularly sugar cane, for the production of carbohydrates, ethanol, and related products, using physico-chemical and extraction techniques, with the adoption of very simple biomass milling configurations, so as to reduce significantly the consumption of energy during extraction of the juice present in the said biomass.

When subjected to a sequential process of saccharification and fermentation, the biomass treated and obtained through the technique of the present invention enables an increase in the production of ethanol in comparison with the conventional process (first-generation ethanol) using sugar cane. This technique can also be used for the production of enzymes, animal feedstuffs, and industrially useful products derived from the conversion of carbohydrates, lignin, and ethanol (first- and second-generation) obtained from plant biomass.

BACKGROUND OF THE INVENTION

Sugar cane belongs to the Poaceae family and can grow to heights of 2.5 to 4.5 meters. It contains 11% to 17% saccharose by weight and 11% to 15% fiber (lignocellulosic material) by weight. The cane is cut, along with the stalk, and is transported by truck to the plant.

The cane is unloaded onto a feed table and either washed with water or dry-cleaned in order to remove earth, debris, and straw. This stage is known as the receipt of the cane.

Preparation and Milling of the Cane

After receipt, the cane goes to the preparation stage, which takes place inside a piece of equipment (the chopper) that consists of knives rotating at high speed (500 to 1200 rpm). The cane is cut into small, short pieces ("cuttings"), which form a compact uniform layer that is then sent to the defibrator. The purpose of this piece of equipment is to encourage a high degree of disintegration of the cane, so as to facilitate the extraction of the sugars during the milling stage. The defibrator consists essentially of hammers that rotate at high speed (500 to 1500 rpm) and that are fastened to a metal plate, through which the cane is forced to pass via a narrow space ranging from 10 to 25 mm, so that the cane cells are "opened" and thereby prepared for the subsequent milling (extraction) stage.

The extraction stage consists of the milling of the cane by means of sets of rollers (three-roller combinations). Each milling unit usually consists of four three-roller milling combinations, by which the cane is pressed (crushed) under high pressure in order to extract the sugars. A typical extraction unit contains from four (4) to seven (7) three-roller milling combinations.

The milling rollers are driven by electric motors, steam turbines, or hydraulic systems. The milling stage typically consumes between 40 and 60% of the total energy required for the production process, thereby characterizing the operation as one with a high energy demand.

The first milling stage results in the production of a stream of liquid (the primary juice) that has a high saccharose content, which is sent for the manufacture of sugar or for the production of first-generation ethanol.

After the second milling stage, the mixed juice is extracted. This mixed juice consists of the juice obtained from the second grinding stage plus the juices produced during the adjacent stages, as well as the water added during the milling stage. Despite having a lower saccharose content and a lower purity level in comparison with the primary juice, this juice can also be used in the production of first-generation ethanol, in addition to being mixed with the primary juice for the production of sugar.

There is currently a growing demand for ethanol on the domestic and foreign markets, thanks to its use as a fuel and as an anti-knock agent in automobile engines. Brazil is the technological leader in the production of so-called "flex-fuel" vehicles, which use ethanol either in pure form or mixed with gasoline. Estimates indicate a significant growth in domestic demand for ethanol, thanks to the total or partial replacement of gasoline in various automotive vehicles. This increase is generating pressure to expand the area in which sugar cane is grown for the production of ethanol, which in turn exacerbates the onset of conflicts associated with land occupancy and land use, as well as the environmental issues inherent in sugar-cane cultivation.

In addition to the use of ethanol as a fuel, its processing as a raw material is awakening increasing interest in the chemical industry. Rising petroleum prices, combined with the non-renewable nature of this resource, illustrate the true feasibility of developing technological platforms such as so-called "biorefineries" that use readily available and relatively inexpensive renewable resources. In this context, the production of ethanol and of other highly worthwhile and industrially applicable chemicals from renewable resources, such as sugar-cane bagasse, has emerged as a potentially attractive alternative technology. In particular, the production of ethanol from the cellulose present in bagasse (i.e., cellulosic ethanol) has awakened a growing interest, thanks to its numerous benefits economic, strategic, social, and environmental benefits.

The process of producing cellulosic ethanol from bagasse requires the conversion of the cellulose into glucose, and the subsequent use of microorganisms to convert the glucose into bioethanol. However, native cellulose is heavily protected by the lignin-carbohydrate matrix, such that the cellulose is very resistant to hydrolytic action, with the result that the processes for converting cellulose into glucose are slow. Due to the association of cellulose with the hemicelluloses and with lignin, the access of several chemical agents (e.g., acids and alkalis) and biochemical agents (e.g., enzymes and microorganisms) used in fermentation-based processes for the production of cellulosic ethanol is substantially restricted. The cellulose matrix is organized in the form of fibers that are joined by hydrogen bridges and Van der Waals bonds, forming a rigid molecular structure (microfibrils) with diameters ranging from 10 to 30 nm. Moreover, the high crystallinity of the cellulose makes it extremely difficult to convert the cellulose into fermentable sugars through the use of hydrolysis processes. The sugars in turn are converted into ethanol. Therefore, ethanol production processes require initial treatment of the biomass (i.e., pre-treatment) in order to "open" the cellulosic matrix to the action of the hydrolysis agents, including, in particular, the enzymes. The regions of low crystallinity (i.e., the amorphous regions) present in the microfibrils are susceptible to enzymatic action, such that pre-treatment of the biomass can be omitted.

Pre-treatment of a lignocellulosic biomass is one of the most significant operational stages in terms of direct cost, and also has a substantial effect on the costs of the preceding and subsequent stages of the process. Basically, pre-treatment relates to the operations for the preparation of the raw material (i.e., grinding and impregnation), as well as to the hydrolysis (acid or enzymatic) of the cellulose (i.e., the loading and consumption of enzymes or acids, and the reaction rates); the generation of products that inhibit enzymatic hydrolysis and alcoholic fermentation; the saccharide concentrations of the resulting hydrolysates; the purification of the intermediate products; the treatment of waste; mechanical agitation; and the generation of energy. Within this context, the proper integration of the various operations must be sought. The performance of a pre-treatment technique must be evaluated in terms of its effect on the costs associated with the preceding and subsequent stages, as well as its effect on the operating costs, the cost of the raw material, and the cost of capital. Accordingly, the pre-treatment per se must be highly efficient in terms of its yield, selectivity, functionality (i.e., ensuring that the cellulose is accessible to the hydrolytic agents), operational simplicity, industrial health and safety, and environmental considerations, while also reducing the consumption of chemical supplies, energy, and utilities. Generally speaking, an efficient pre-treatment of sugar-cane bagasse for the production of ethanol should produce a cellulosic pulp whose fibers are readily accessible and responsive to the acidic or enzymatic hydrolytic agents (i.e., a pulp whose fibers possess the property of digestibility) and also ensure adequate recovery of the pentoses, while simultaneously limiting the generation of compounds that inhibit the enzymes and the microorganisms that are used in the fermentation process. Eco-efficient pre-treatment systems are also characterized by factors associated with the use of inexpensive catalysts, the recycling of consumable materials, and the generation, from the lignin, of byproducts having a high added value.

Although several pre-treatment techniques are potentially applicable to sugar-cane bagasse, comparative studies based on the data available in the literature are particularly difficult, because of the differences in the research methodologies, in the physical characteristics of the material, and in the methods for the preparation of the raw material. However, attention must be paid to the importance of improving and expanding the level of knowledge about the various types of pre-treatment, as well as about the effect of each process on the other operations. Such a step can facilitate the selection of equipment and of the operational sequences of the system as a whole, and reduce the risks associated with the implementation of the process on an industrial scale. It can also reveal opportunities for improvement throughout the integrated system, thereby leading to the optimization of operational efficiency while minimizing the overall costs of ethanol production.

Various methods for the pre-treatment of lignocellulosic plant biomasses have been suggested over the course of the last two decades. They can be divided into physical methods, chemical methods, biological methods, and combinations thereof. The physical methods (e.g., pelletization and milling) convert the biomass into fine powder, increasing the specific surface area of the cellulose, such that its hydrolysis is relatively easy. The major disadvantage of this method is its high energy consumption. For bagasse, the milling of the cane can be viewed as an operation for the pre-treatment of the fiber. Irradiation of the cellulosic fiber with gamma rays breaks the β-1,4 glycosidic bonds of the cellulose. The result is an increase in the specific surface area and a reduction in the crystallinity of the cellulose, such that its hydrolysis rate tends to increase. However, this method is considered too expensive to be implemented on an industrial scale. The option consisting of pre-treating the biomass by pyrolysis requires the use of very high temperatures (greater than 300° C.), causing rapid decomposition of the cellulose, but with the production of gaseous compounds and the formation of tarry residues. Acid hydrolysis of the solid fraction under moderate conditions converts the cellulosic fragments into glucose. Despite its relative operational simplicity, the overall efficiency of pyrolysis of the lignocellulosic biomass is low, because of the high saccharadic losses and the reduced glucose selectivity, in addition to the formation of fermentation-inhibiting compounds. The physico-chemical pre-treatment processes that use diluted acid, high-pressure steam, or hot water allow the selective removal of the hemicelluloses, producing (pre-hydrolyzed) saccharidic solutions with a high pentose content and a reduced lignin content. Alkaline processes tend to encourage greater dissolution of the lignin and less solubilization or fragmentation of the hemicelluloses.

Although many treatment methods have been the subject of experiments in recent years, there is a growing need to develop alternative technologies that are efficient in terms of overall cost and economic competitiveness. Basically, selective extractions of non-cellulosic components (i.e., lignin and the hemicelluloses) have been achieved at relatively modest costs through the use of alkalis or acids. In particular, pre-treatments using water steam, dilute sulfuric acid, ammonia, and calcium hydroxide (i.e., lime) have emerged as some of the most promising options. Table 1 shows some of the operational conditions used in different pre-treatments of biomasses, such as sugar-cane bagasse and corn stover.

There are similarities between the major methods involving the acid pre-treatment of the biomass (e.g., hot water, steam explosion, and hydrolysis with dilute acid) for the production of ethanol, because all of the methods are based on the combined action of water and the hydronium cation ($H^+$) in different proportions and at different severity levels in the process.

The pre-treatment known as "steam treatment" (often referred to as the "steam explosion" method), which originated in the Masonite process used in the manufacture of pressboard, is one of the most widely used methods for converting lignocellulosic plant biomasses. When a lignocellulosic material is heated to relatively high temperatures with saturated steam, followed by the sudden decompression of the equipment, a brown slurry resulting from the fragmentation of the biomass is produced. After the material is washed, the liquid is separated, and adhesives are added, the pressboard is produced. In Brazil, certain companies have used sugar-cane bagasse in the production of pressboard products for the furniture industry.

Pre-treatment with steam has chemical and physical effects during the conversion of the lignocellulose, with the chemical reactions predominating. The biomass is treated with saturated steam at a temperature of 160° C. to 240° C. (at pressure of approximately 6 to 34 bar) during a reaction time of 1 to 15 minutes. After this period, decompression is applied to the system, and the material is collected in an expansion tank (also known as a "flash tank" or "blow tank"). During the steam treatment of the biomass, the hemicelluloses are idolized, and certain bonds between the cellulose and lignin are broken. The structure of the biomass becomes more susceptible to penetration by the water, acids, and enzymes, such that the hydrolytic potential of the cellulose is increased. The carbohydrates released from the hemicelluloses may suffer thermal degradation, while the lignin may undergo partial fragmentation and be dragged to the hydrolysate. The breakdown products that are produced may have an inhibitory effect on the subsequent operations. Hydrolysis in steam treatments may be catalyzed by organic acids (e.g., acetic acid) formed by the splitting of the functional groups present in the hemicelluloses. In such cases, autohydrolysis of the hemicelluloses (which is a characteristic of autocatalytic processes) is observed. Catalyst acids ($SO_2$ and $H_2SO_4$) and Lewis acids ($FeCl_3$, $ZnCl_2$) can be used, which lead to an increase in the recovery of hemicelluloses sugars, as well as facilitating, during the subsequent stages, the hydrolysis of the cellulose present in the pre-treated pulp. The pre-treatment of biomasses that contain a high level of highly acetylated hemicelluloses (as is the case with bagasse) requires minimal quantities of catalyst acids. Thus, the use of these catalyst acids has an effect similar to that of chemical pre-treatment with dilute acid, while requiring a much smaller amount of liquid. Moreover, steam pre-treatment is similar to the hydrothermolysis ("hot water") process, but larger loads of solids can be used in steam pre-treatment. This method is particularly worthwhile, given that it offers advantages associated with greater concentration of the hydrolysates, lower water consumption, and the generation of fewer liquid effluents. Steam pre-treatment can be viewed as a process that employs a mature technology, such that, of the methods described here, it is the closest to commercial implementation.

Hydrothermolysis (the "hot water" method, also known as "solvolysis" or "aquasolv"), uses compressed water in contact with the biomass for 1 to 15 minutes at temperatures between 170° C. and 230° C. At these temperatures, the water promotes the cleavage of the hemiacetal bonds of the carbohydrates, releasing acids during the hydrolysis of the biomass. In this process there is no need to reduce the size of the biomass particles, which tend to break up upon contact with the water during the so-called "cooking" process. Approximately 40% to 60% of the biomass is dissolved during the process, with the cellulose removal ranging from 4% to 22%. More than 90% of the hemicelluloses are recovered when acid is used as a catalyst for the hydrolysis of the resulting liquid; however, reduced saccharide concentrations, on the order of 0.5 to 6.0 g/liter, are obtained. Flow-through reactors and batch reactors can be used, in countercurrent and co-current configurations. In flow-through reactors, the hot water passes through a stationary biomass bed, thereby encouraging the hydrolysis of the lignocellulosic components, which are carried out of the reactor. Large quantities (35% to 60%) of lignin are removed during this process. Generally, because of the solubilization of the lignin, the use of special separation systems is required for suitable recovery of the hemicelluloses. Cellulosic pulps with a high level of fiber reactivity are typically produced, and the hydrolysate produced during the hydrolysis of these pulps tends to display adequate fermentability in ethanol. The use of catalyst acids makes the hot-water method similar to pre-treatment with dilute acid.

However, the hot-water process has major disadvantages in comparison with the steam-explosion system. Smaller loads of solids (e.g., 1% to 8%) must be used, because of the formation of inhibitors in the hydrolysates that are produced when solids concentrations greater than 10% are used. The amount of water used in the hot-water process is usually much larger than the amount used in the steam-explosion process, thereby producing very dilute hydrolysates, which tends to cause operational problems during the subsequent stages of the overall system. It should be pointed out that when hydrolysates are used as an agent for the dilution of molasses in fermentation systems that use microorganisms that convert pentoses, this problem is smaller and less important.

The hydrolysis process with dilute acid has been used industrially in the production of furfural, serving as a potentially worthwhile technological option for the pre-treatment of lignocellulosic biomasses. Basically, the hemicelluloses are removed, thereby producing pulps with a high level of fiber reactivity. Although sulfuric acid is customarily used as the hydrolytic agent, other acids (e.g., nitric, hydrochloric, and phosphoric acid) may also be used.

Basically, the mixture (i.e., the solution consisting of the acid and the biomass) may be heated indirectly in the reactor or directly through the injection of steam, in which case it bears some resemblance to the steam-explosion system. The acid is added to the liquid and percolates through the stationary biomass bed, after being sprayed onto the mass or even mixed with the biomass by means of mechanical stirring. The use of sulfuric acid has some drawbacks, such as corrosion of the equipment and the need to neutralize the resulting liquid (i.e., the hydrolysate), in addition to the formation of fermentation inhibitors. It should be emphasized that, thanks to the relatively easy removal of the hemicelluloses from the bagasse, the processes that use dilute acid can be implemented under relatively moderate processing conditions (e.g., 160° C. to 170° C.), with reduced formation of these inhibitors, while pulps with reactive fibers are obtained. The hydrolysis processes that use dilute acid require a raw material with a low ash content and low levels of other impurities, because of the buffering effect of such substances, which leads to a high consumption of acid. Washing the biomass prior to the pre-treatment is necessary in order to prevent this problem.

Pre-treatment processes with dilute acid in flow-through reactors use $H_2SO_4$ at concentrations on the order of 0.05% to 0.07%, which are much lower than the concentrations used in batch systems (i.e., 0.7% to 3.0%). Moderate temperatures (140° C. to 170° C.) are used in the first stage, the hydrolyze the most reactive hemicellulose fraction, whereas in the second stage more severe conditions (180° C. to 200° C.) are used, in order to hydrolyze the more recalcitrant hemicelluloses. Approximately 30% to 50% of the lignin is extracted, whereas approximately 80% to 95% of the hemicelluloses (predominantly in the form of monomers) are recovered. The pre-treated pulp has a high level of fiber reactivity, with enzymatic digestibility on the order of 90%. However, the process requires complex equipment configurations, in addition to an elevated hydromodule and high levels of water and energy consumption.

In comparison with the acid systems, the alkaline pre-treatment processes typically use moderate operating conditions in terms of temperatures and pressures. The major effect of the pre-treatment consists of the removal of the lignin from the biomass, thereby promoting a higher level of reactivity of the fiber. The alkali (usually sodium hydroxide or lime) tends to cause swelling of the biomass, so that the crystallinity of the cellulose decreases, while the specific surface contact area and the porosity of the cellulose both increase. The lignin-carbohydrate bonds are broken, and the structure of the lignin is fragmented. In some cases, the pre-treatment can be performed at room temperature. However, relatively lengthy reaction times are required, on the order of hours or even days. Unlike the acid systems, one major limitation of the alkaline processes consists of the need to recover the alkalis, so as to ensure that the process is appropriately economical. Because the alkaline processes cause substantial delignification of the biomass, these system should preferably be used in the pre-treatment of materials that have a low lignin content (e.g., agro-industrial wastes), with a view toward minimizing the amount of lignin present in the hydrolysate. The alkaline pre-treatment techniques under consideration for the production of ethanol are currently being tested only at the laboratory level and in pilot units.

The pre-treatment of bagasse using calcium hydroxide (i.e., lime) has certain advantages in terms of the cost of the reagent, the safety of the process, and the possibility of recovering the alkali in the form of calcium carbonate, through a reaction with the carbon dioxide produced during the alcoholic fermentation stage. The carbonate can then be converted into the hydroxide, through the use of established conventional industrial techniques. The addition of oxygen or air (as in so-called "wet alkaline oxidation") tends to result in lignin removal on the order of 80%. However, such processes produce hydrolysates with a high lignin content, such that the use of lignin-carbohydrate separation systems is required for recovery of the hemicelluloses.

The wet alkaline oxidation process consists of treating the biomass with water and oxygen at temperatures above 120° C. A variant of the method, known as "wet alkaline peroxide oxidation," consists of using $H_2O_2$ as the oxidizer, with reaction times on the order of 2 to 8 hours at temperatures between 30° C. and 70° C. Sodium carbonate, calcium hydroxide (i.e., lime), or sodium hydroxide is generally used as the hydrolysis and delignification agent.

Oxidative alkaline pre-treatments produce pulps with a high level of fiber reactivity, due to the accessibility of the cellulosic matrix to the enzymes. However, a large amount of lignin is oxidized and solubilized during these processes, so that it cannot be used as a fuel, thereby compromising the energy efficiency of the overall system. Furthermore, certain fermentation inhibitors (e.g., organic and phenolic acids) are formed in the hydrolysates that are produced, thereby compromising the subsequent stages.

The AFEX ("Ammonia Fiber Explosion") process is the alkaline version of the steam-explosion pre-treatment process. Basically, there is an increase in the reactivity of the cellulosic fraction, due to its swelling, combined with the hydrolysis of the hemicelluloses and the disintegration of the fiber. The biomass is subjected to the effect of liquid ammonia (at a ratio of 2 kg per kg of biomass) at a temperature of 160° C. to 180° C., at pressure of 9 to 17 bar, for a period of 10 to 20 minutes. Then the pressure in the system is rapidly released, and the "exploded" material is collected in the flash tank. The advantages of this method include the high level of reactivity of the fiber, the minimal generation of fermentation-inhibiting compounds, and the recovery of the ammonia. However, the AFEX method does not promote the high level of hemicellulose solubilization that occurs in the acid processes, allowing the hemicelluloses to be recovered in the resulting hydrolysates. The SHFEX ("Sodium Hydroxide Fiber Explosion") process uses sodium hydroxide under similar conditions, but with advantages associated with the recovery of the alkali, in addition to greater safety of the process. However, both processes produce hydrolysates with a high lignin content, such that the use of lignin-carbohydrate separation systems and recovery of the alkali are necessary.

Pre-treatment systems that use $CO_2$ as an hydrolysis agent (e.g., the "$CO_2$ Explosion" and "Supercritical $CO_2$" systems) can be viewed as potentially worthwhile long-term technological options for the pre-treatment of sugar-cane bagasse, using the $CO_2$ produced during the alcoholic fermentation stage. Basically, the $CO_2$ is converted into in situ carbonic acid, such that the hydrolysis of the hemicelluloses is substantially increased. In economic terms, this method is more efficient than the AFEX process, in addition to not producing the fermentation inhibitors that are generated during steam pre-treatment. However, pre-treatment with $CO_2$ has been less efficient than the other methods, in terms of the production of pulps with a high level of fiber reactivity. The pre-treatment of bagasse impregnated with 0.05% $H_2SO_4$, using supercritical $CO_2$, allows satisfactory recovery of the hemicelluloses, on the order of 82%; however, the pre-treated pulp tends to display enzymatic digestibility of only 50%.

Based on the foregoing description, various solutions have been proposed and protected with a view toward energy savings in the production of ethanol.

U.S. Pat. No. 4,326,063 [sic] describes an integrated process for the production of ethanol, in which the sugar cane is cut and triturated so as to produce a mass of fiber and juice, which is then digested enzymatically in order to convert the contents of the fibers into fermentable sugar. The digestion product is then separated into a fibrous residue and a liquid fraction containing the sugars.

The fibrous residue then undergoes a second enzymatic digestion process combined with fermentation, thereby generating a new fibrous residue and a new, partially fermented liquid fraction, which are then separated.

The liquid fractions are then combined and fermented for the production of ethanol, which is then recovered.

This dual digestion of the sugar cane is the key factor for the economic management of the process, by ensuring that a majority of the fermentable material is extracted from the sugar cane and that this bagasse is burned in order to generate energy during the process.

In U.S. Pat. No. 4,356,196, alfalfa and other plants are treated with ammonia at high pressures, to increase their digestibility and protein availability. The cellulose can also be broken down enzymatically to produce glucose, which is then converted into ethanol through conventional processes.

U.S. Pat. No. 5,037,663 describes a process for increasing the chemical and biological reactivity of cellulose and/or hemicellulose in animal feedstuffs. This process involves placing the material in a pressurized vessel and bringing it into contact with a volatile agent, such as ammonia, whose vapor pressure is greater than atmospheric pressure at ambient temperatures. Contact is maintained for a period sufficient to allow the agent to swell the cellulose of the material. The pressure is then rapidly reduced to atmospheric pressure, causing the boiling of the agent and the explosion of material.

Similar treatments are described in U.S. Pat. Nos. 6,416,621, and 7,189,306, and in U.S. documents No. 2008/0008783, No. 2007/0031953, No. 2007/0031918, and No. 2007/0031919.

The present invention differs from these documents in that it provides energy savings through the use of a stage consisting of the milling of the biomass, particularly sugar cane, using a smaller number of three-roller milling combinations, without fully exhausting the cane juice and with a stage consisting of subjecting the cane resulting from the said milling to a less severe chemical treatment.

With regard to another aspect, U.S. Pat. No. 5,266,120 describes a process for the chemical pre-treatment of sliced sugar beets, in which the sliced sugar beets are placed on a line and soaked with a cold solution of calcium monosaccharide in order to fix this compound on the said slices. The patent provides a circulation system in which the byproducts formed by the breakdown of the calcium compound and the subsequent reaction with the sugars from the sugar beets are avoided.

U.S. Pat. No. 5,772,775 describes how, in order to achieve an efficient juice-extraction process, compaction of the bed should be avoided, so as to prevent low rates of percolation and expulsion of the juice. Accordingly, ages-extraction process that includes stages consisting of air displacement and the displacement of the juice from the fibrous material by means of a so-called "plug-flow" (tubular reactor) process, with the removal and separation of the juice.

The present invention differs from these documents, in that it teaches an integrated process for the treatment of the biomass, which consists of a mechanical stage (i.e., defibration and milling of the biomass), in conjunction with a subsequent stage involving the physico-chemical treatment of the resulting lignocellulosic material.

As mentioned hereinabove, the processing of cane sugar in juice-preparation and juice-extraction systems constitutes an operational stage that involves a level of energy consumption that is significantly substantial within the context of the overall energy balance of the integrated production system (for both sugar and ethanol). In this setting, the use of ages-extraction system that contains a shorter series of stations (i.e., preparation areas and three-roller milling combinations) enables significant energy savings, thus characterizing an eco-efficient system. Furthermore, the simplification of the extraction process tends to produce fibrous fractions (i.e., bagasse) containing higher levels of saccharose.

The use of bagasse pre-treatment processes implemented under severe conditions (i.e., high temperatures and pressures) tends to increase considerably the breakdown of the saccharose and other carbohydrates present in the biomass, resulting in a loss of production and a lower ethanol yield. In this context, the development of an extraction system associated with a pre-treatment process conducted under moderate conditions (i.e., less severe conditions) enables a significant increase in the energy efficiency of the integrated system for the production of sugar and first-generation ethanol. Furthermore, the reduced energy demand results in a smaller amount of bagasse burned in the boiler for the production of steam and energy, thereby increasing the availability of this biomass for the production of cellulosic ethanol and other products of industrial value.

In short, based on all of the foregoing considerations, it can be said that the current state of the art does not anticipate or suggest the teachings of the present invention, which recommends the development of a simplified system for the preparation of sugar cane and the extraction of juice with less energy consumption (in comparison with the conventional system), in conjunction with a process for the pre-treatment of the lignocellulosic material (including, in particular, the bagasse), with a view toward the production of sugar (and other carbohydrates), first-generation ethanol, cellulosic ethanol (i.e., second-generation ethanol), as well as other products of potential industrial value.

SUMMARY OF THE INVENTION

First of all, the present invention provides a more efficient and less energy-costly process for the treatment of plant biomass, which process can increase the availability of the sugars and make use of the biomass in a much more advantageous way than can be done with the treatments in the prior art.

One goal of the present invention consists of a process for the treatment of plant biomass that includes the stages consisting of:

a) Defibration of the plant biomass;
b) Optional extraction of part of the juice by grinding or diffusion, with the grinding including up to 3 three-roller milling combinations; and
c) Treatment of the solid defibered plant biomass from stage (b) with chemical agents at different levels of severity (S), within the range from 3.16 to 4.28.

A further goal of the present invention consist of the conversion of the treated biomass, as obtained through the technique described hereinabove, in which a majority of the Total Reducing Sugars (TRS) is processed, in contrast to the traditional process (which is based solely on the production and conversion of saccharose), thanks to the availability of the other carbohydrates present in the biomass, including, in particular, glucose and xylose, as obtained from the cellulose and from the hemicelluloses present in the solid fraction (i.e., the bagasse) of the sugar-cane biomass.

The goals of the present invention are characterized in the following detailed description.

BRIEF DESCRIPTION OF THE FIGURES

FIGS. 1 through 4 describe approaches in which defibration and milling are used, while FIGS. 5 through 8 describe approaches in which defibration alone is used. There is a vast myriad of products and processes that can be configured and produced through the various productive arrangements, along with the use of techniques that involve physico-chemical processes (i.e., pre-treatments) and biochemical processes (e.g., enzymatic hydrolysis and fermentation) which, for example, encourage the production of carbohydrates (e.g., saccharose, glucose, and xylose), enzymes, and first- and second-generation ethanol, as well as carbohydrate derivatives (e.g., organic acids, polyols, and glycols). Likewise evident is the possibility of performing thermal, chemical, and thermo-chemical conversions of the solid residue (i.e., cellulignin) produced during the integrated process in a biorefinery setting, thereby enabling the generation of energy (through combustion), the production of liquid and gaseous fuels (through pyrolysis, gasification, and Fischer-Tropsch reactions), and the production of chemical specialty products having a high added value (through the oxidation of the lignin and carbohydrates).

DETAILED DESCRIPTION OF THE INVENTION

Figure 1:
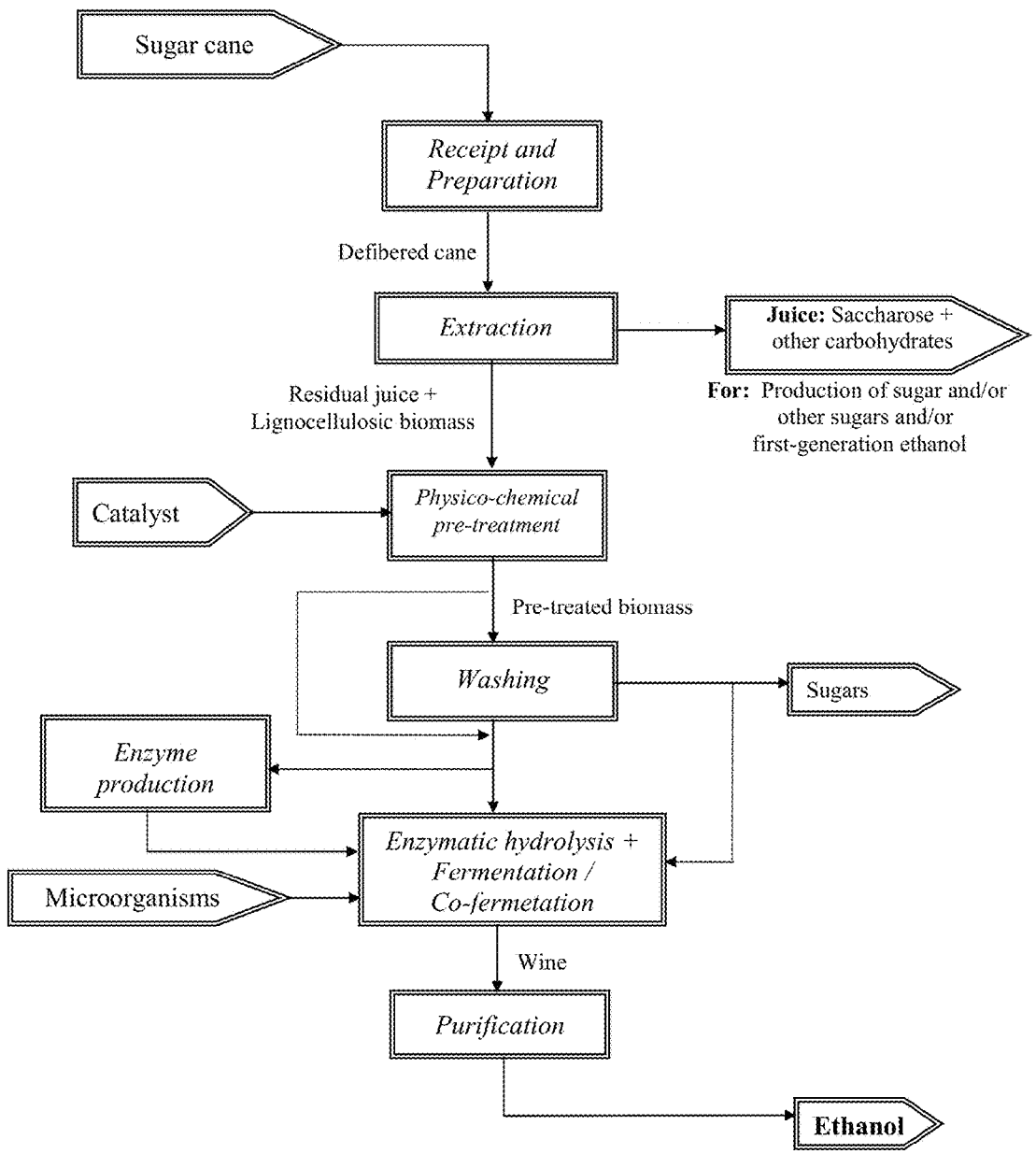
FIGS. 1 through 8 describe the various possible chemical and biochemical approaches pertaining to the integrated systems that are addressed in the present invention.
Figure 2:
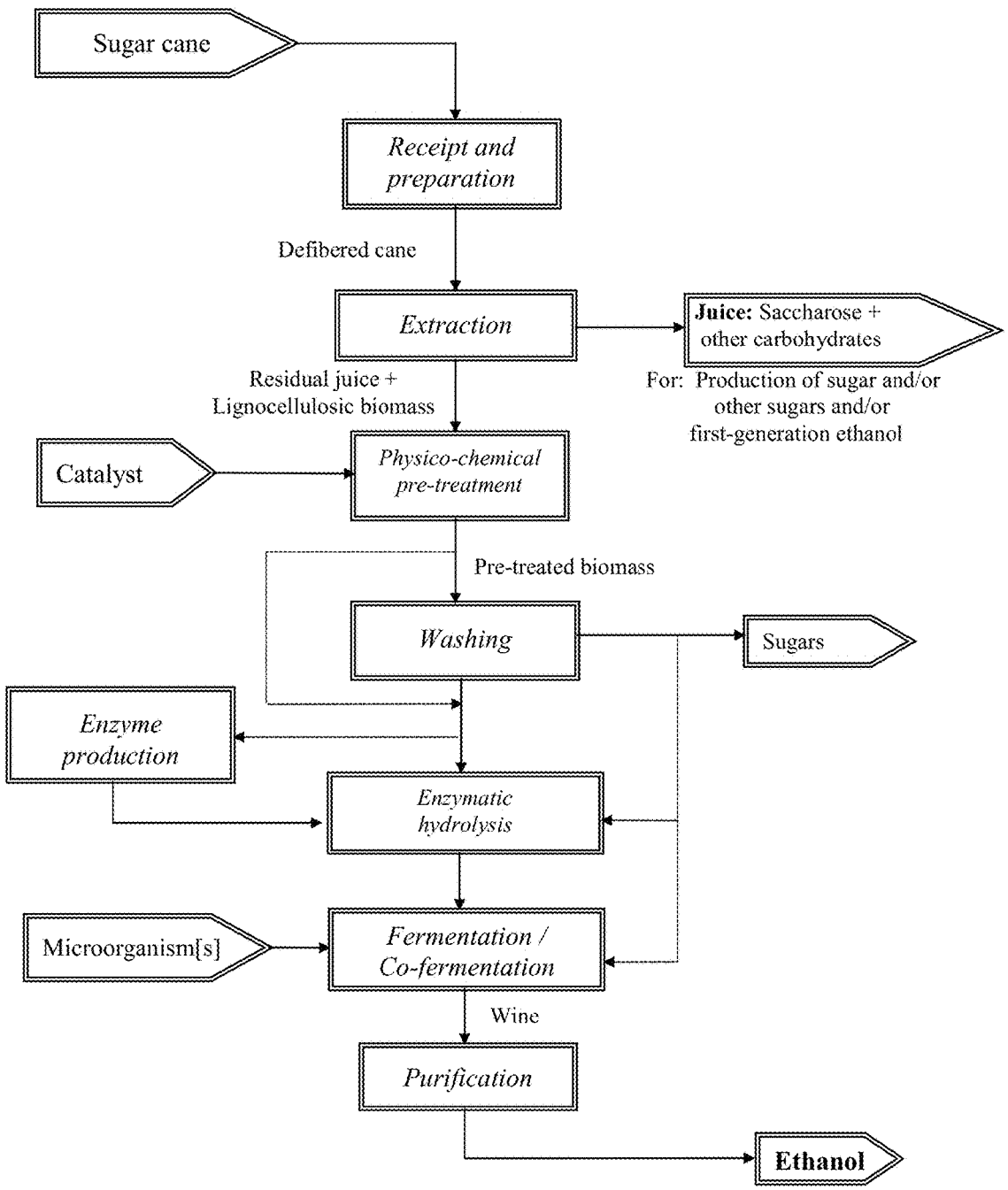
Figure 3:
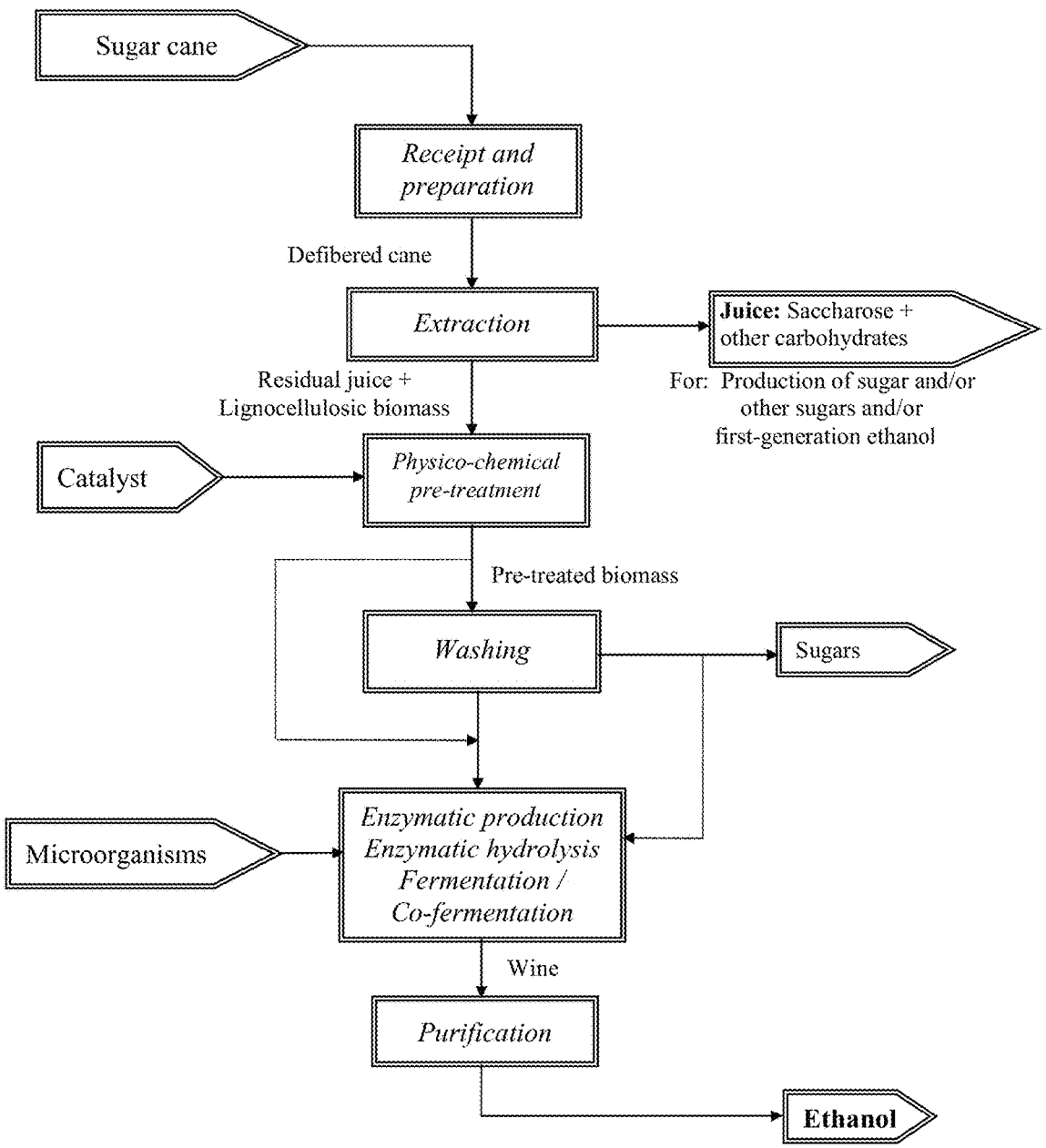
Figure 4:
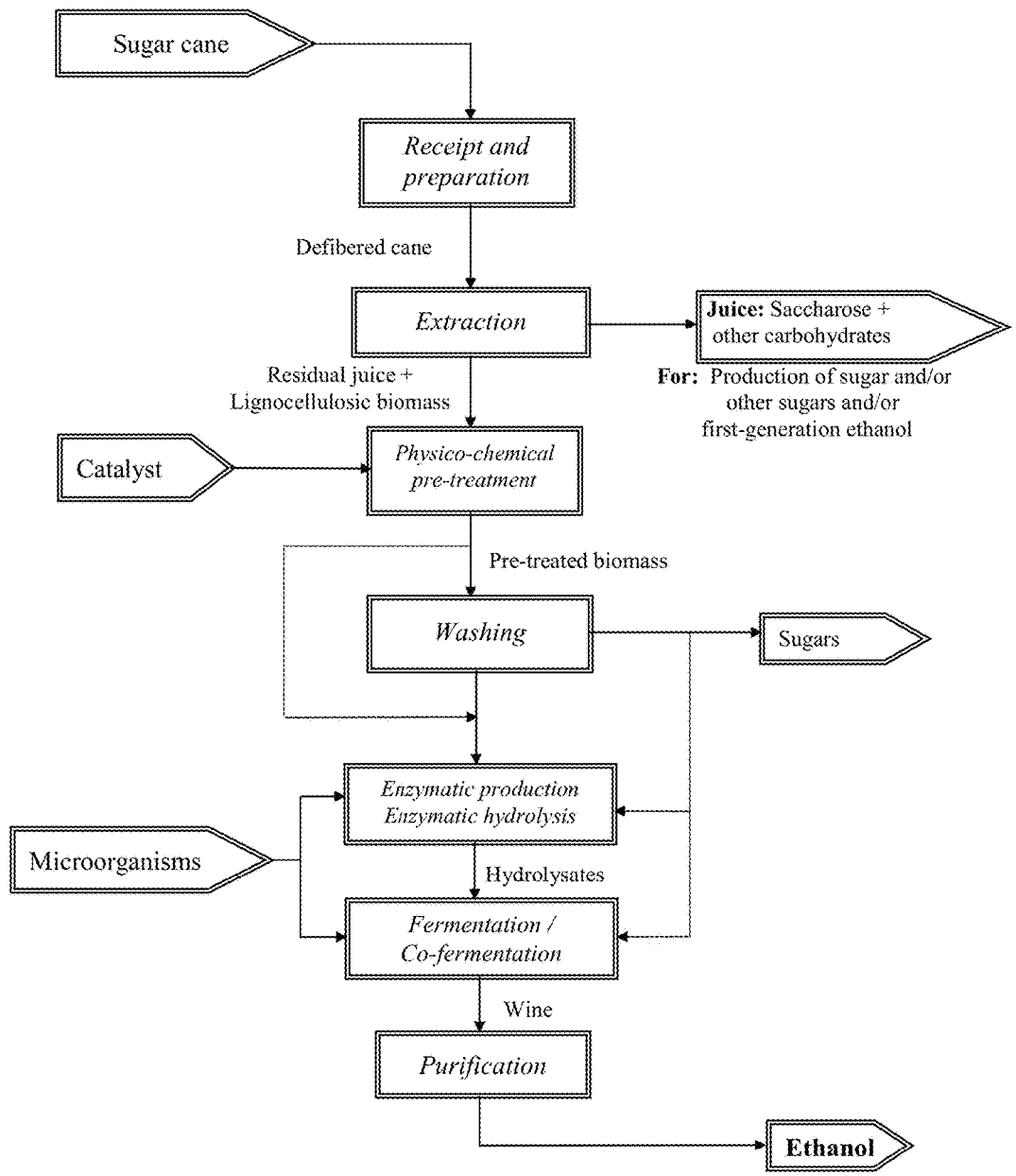
Figure 5:
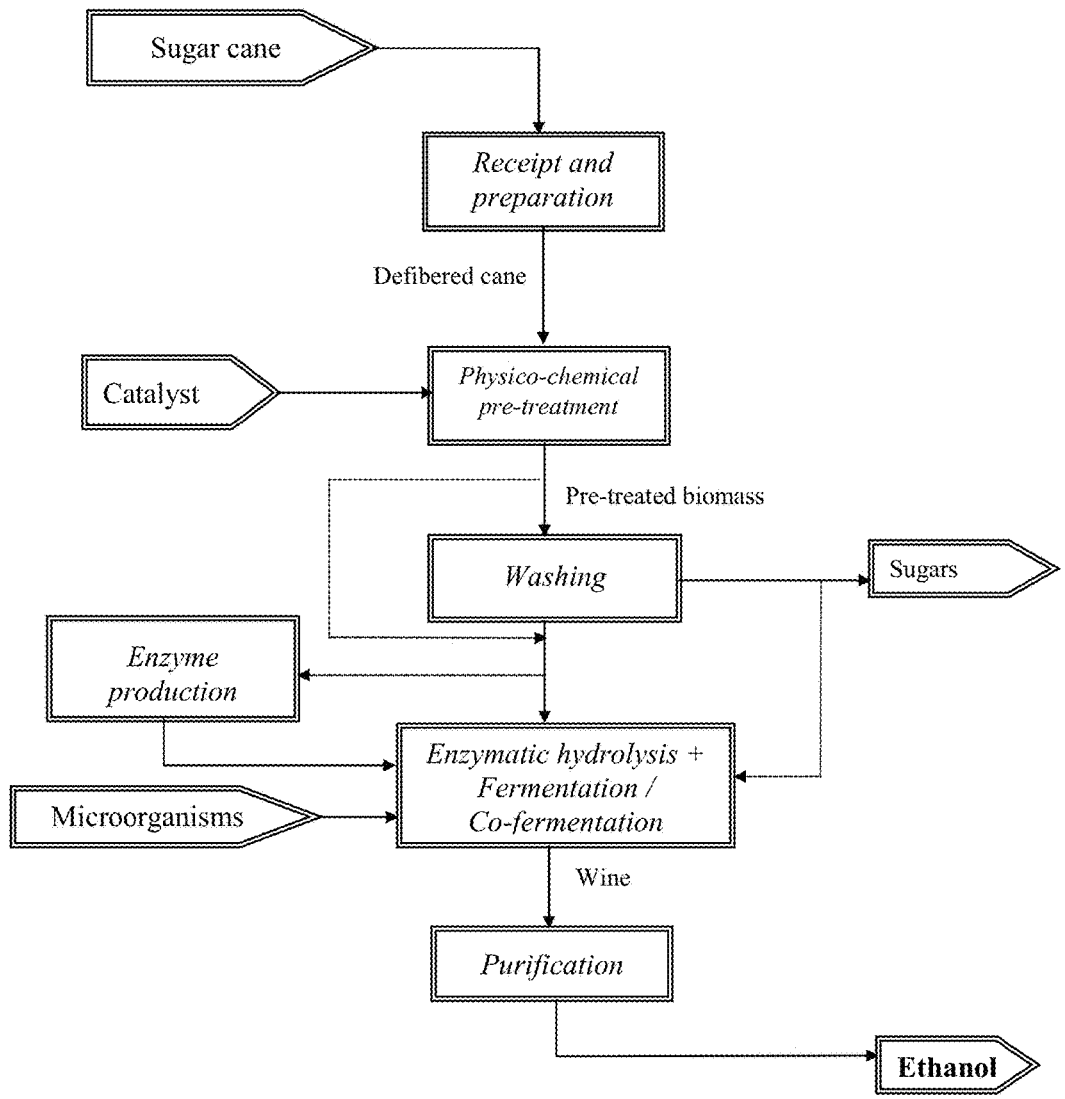
Figure 6:
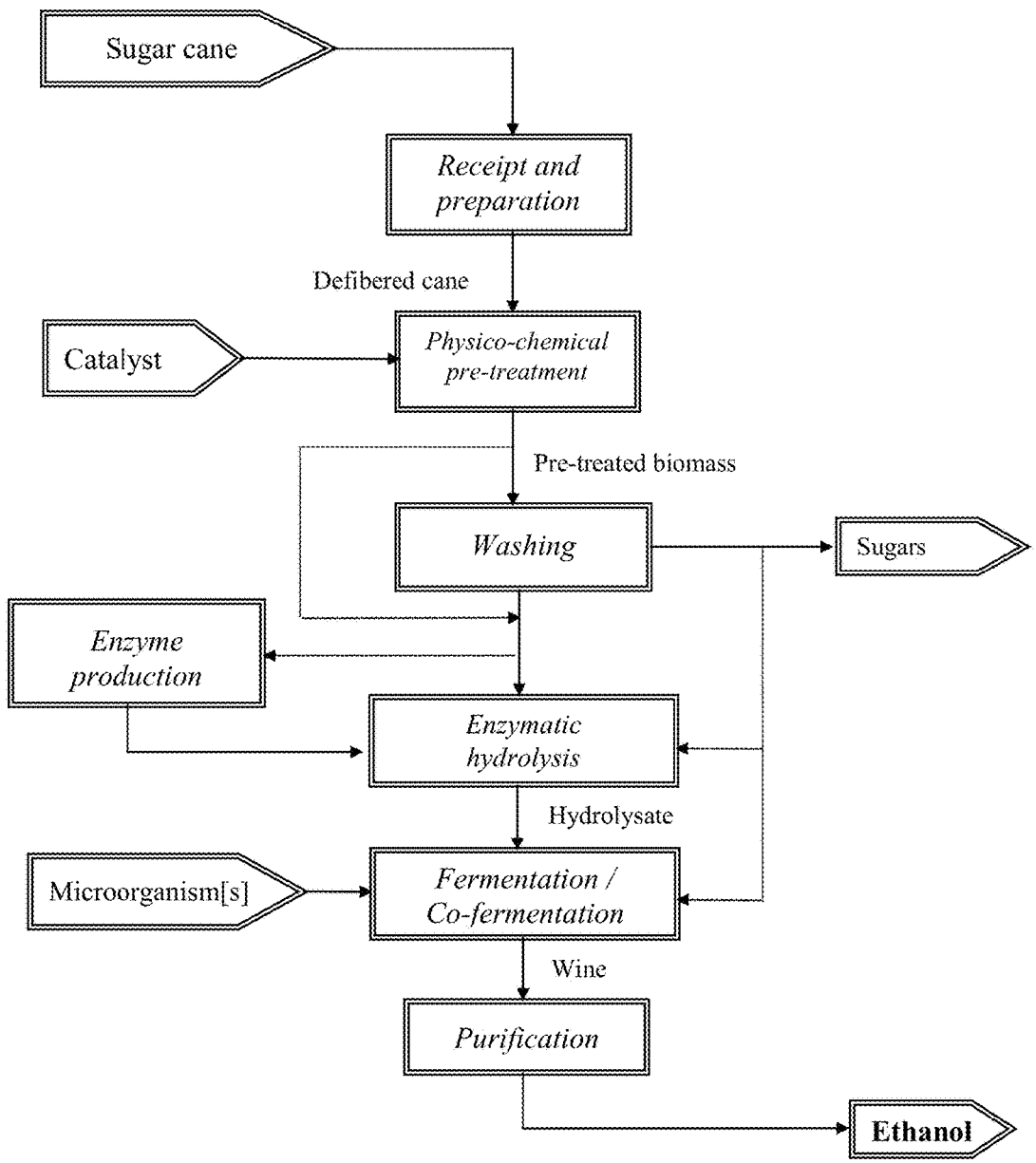
Figure 7:
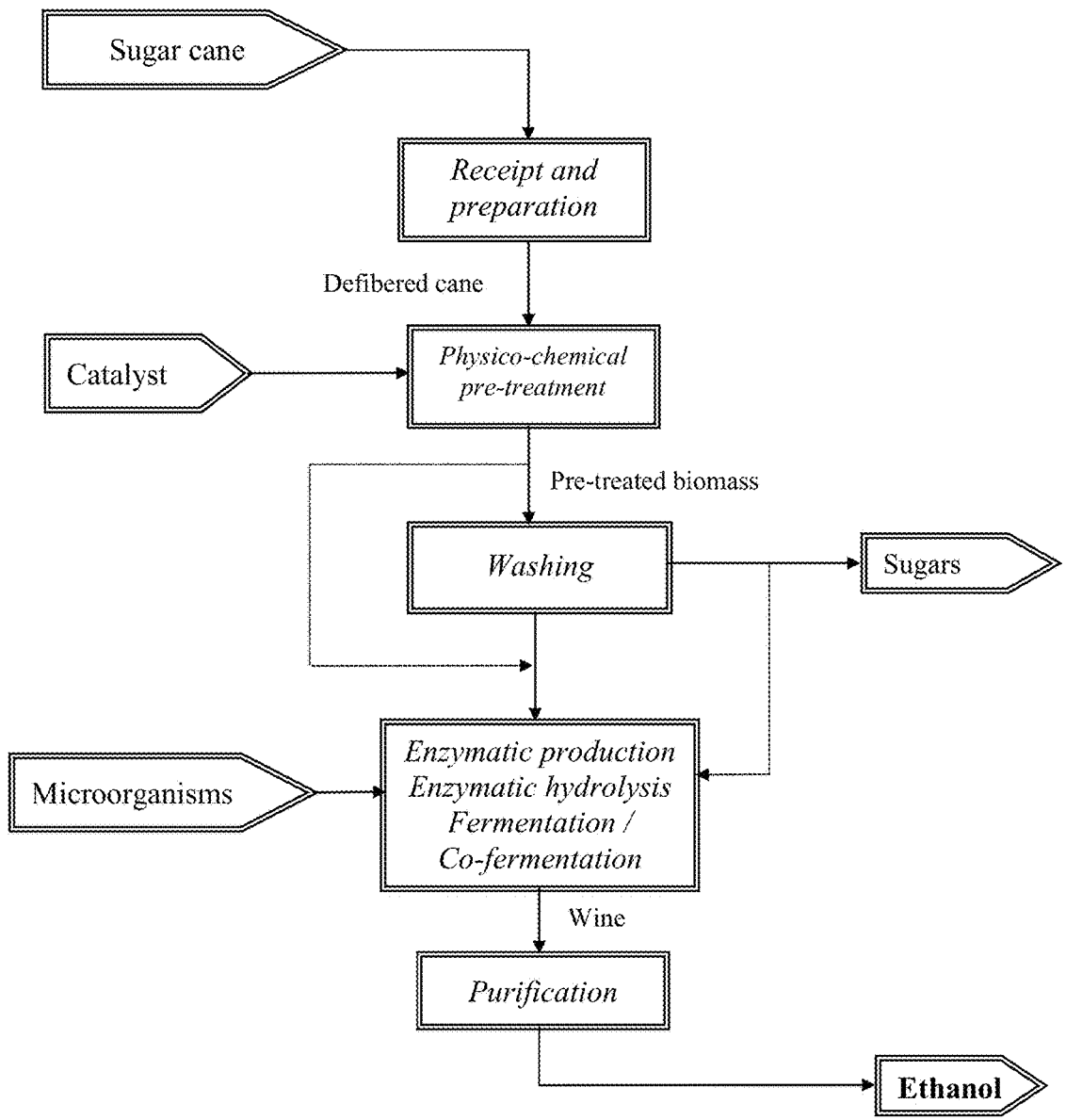
Figure 8:
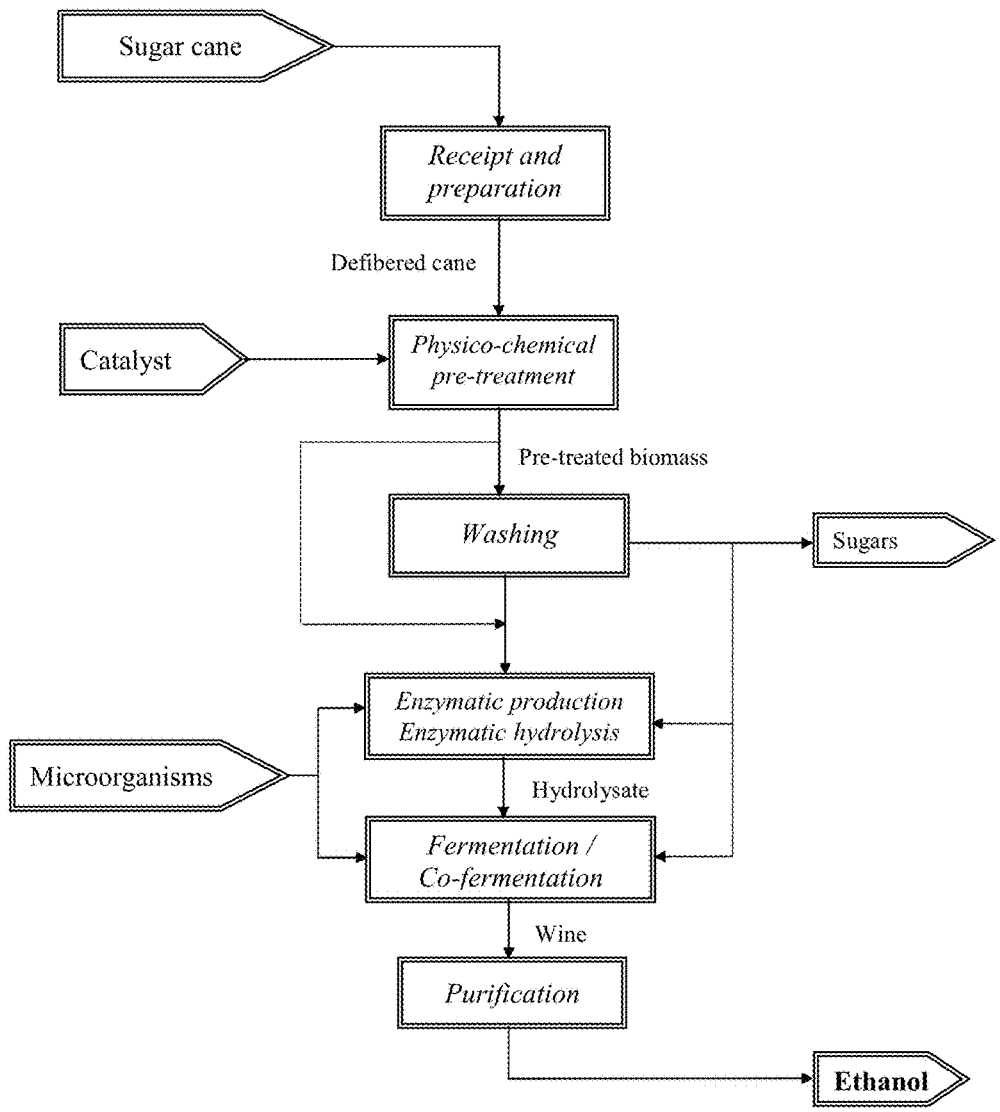

The purpose of the examples described here is solely to illustrate the goals of the invention, and not to limit its application.

Lignocellulosic Plant Biomass

The term "lignocellulosic plant biomass" covers all types of plants, namely, herbaceous biomass; crops such as C4 plants belonging to the *Lolium, Spartina, Panicum*, and *Miscanthus* genera, and combinations thereof; sugar cane, including bagasse (produced by the mill and/or by the diffuser, with bagasse from the diffuser being preferred); straw from cereal crops such as wheat, rice, rye, barley, oats, corn, and similar cereal crops (e.g., elephant grass (switch-grass); wood; banana-tree trunks and stems; cacti, and combinations thereof. Lignocellulosic materials may also consist of cardboard, sawdust, newsprint, and similar agro-industrial or municipal wastes.

Plant biomasses of different origins may display individual differences, even if their overall chemical composition is relatively similar. Some variations in composition between different species, and within a single species, are due to environmental and genetic variability, as well as to the location of the plant tissue in different parts of the plant. Typically, approximately 35% to 50% of the plant consists of cellulose; 20% to 35% consists of hemicelluloses; and approximately 20% to 30% consists of lignin, while the remainder consists of smaller quantities of ash, soluble phenolic compounds, and fatty acids, as well as other constituents, known as "extractives." The cellulose and the hemicelluloses in plant tissue consist of structural carbohydrates (e.g., glycans, xylans, and mannans), which are generally referred to as the saccharide fraction. Lignin is part of the phenolic fraction of plant biomass.

The Pre-Treatment Process

The present invention consists of the development of an extraction system associated with a pre-treatment process implemented under moderate conditions (i.e., conditions of reduced severity). Basically, it includes a process for the treatment of plant biomass by means of a sugar-cane defibration stage, followed by extraction of the sugar-rich juice from the plant biomass by means of milling or diffusion, supplemented by the (pre-)treatment of the plant biomass, as defibered and extracted (i.e., the bagasse) with chemical agents, within the context of the subsequent stages consisting of saccharification (i.e., the production of carbohydrates) and the conversion of the newly available carbohydrates through fermentative processes, for example, for the production of second-generation ethanol, in addition to the production of other products derived from the chemical and biochemical conversion of the carbohydrates that have been produced.

In a preferred embodiment of the invention, the process includes the stages consisting of:

a) Defibration of the plant biomass;
b) Optional extraction of part of the juice by milling or diffusion, with the milling including up to 3 three-roller milling combinations; and
c) Treatment of the solid defibered plant biomass from stage (b) with chemical agents at different levels of severity (S), within the range from 3.10 to 4.50.

Defibration

During the dehydration stage, the sugar-cane biomass is placed in a blade mill or knife mill (chopper), or a similar piece of equipment, such that there is a substantial increase in the exposed area (i.e., the contact surface) of the biomass, thereby maximizing the impregnation by the water of imbibition used in the extraction stage, as well as by the physico-chemical agents used in the pre-treatment stage. Satisfactory defibration provides satisfactory imbibition of the sugar cane, thereby promoting greater efficiency and a higher extraction yield of the juice during the milling stage, with a resulting increase in the production of sugar and of first-generation ethanol.

Extraction

The defibered sugar cane is treated and then placed in an extraction unit consisting of a maximum of 3 (three) three-roller milling combinations, and preferably 2 (two) milling combinations, in which the milling of the defibered sugar cane takes place in the presence of water of imbibition, so as to produce a liquid fraction (juice) and a solid fraction (the sugar-cane bagasse).

In comparison with the conventional system, which uses 4 or 5 three-roller milling combinations, the simplified configuration of the equipment, as reflected here by the smaller number of rollers (i.e., three-roller milling combinations), embodies a substantial reduction in energy demand, due to the lower need for power to drive the three-roller milling combinations. Consequently, the lower energy demand results in a significant reduction in the amount of bagasse burned in the boiler (for the production of energy), thereby increasing the availability of this biomass for conversion into sugars and into second-generation ethanol. For example, a reduction of approximately 60% can be obtained in the energy demand of the extraction operations, which represents an overall energy saving (as well as processed bagasse) that, with the configuration adopted in the present invention, is potentially greater than 40%.

Moderate Treatment

After the defibration and milling stages, the solid fraction (i.e., the bagasse) undergoes a moderate (i.e., less severe) pre-treatment, with a view toward making available the carbohydrates that are present in the cellulose and hemicellulose fractions, including, in particular, glucose and xylose, within the context of the subsequent conversions (e.g., purification, hydrogenation, and fermentation), with a view toward the production of second-generation ethanol (i.e., cellulosic ethanol) and other products, for example. Thanks to the presence of residual carbohydrates in the biomass (including, in particular, the saccharose derived from the milling process), moderate processing conditions (e.g., temperature, pressure, and reaction time) must be employed, along with chemical agents such as catalysts (e.g., ammonia, ammonium hydroxide, and sulfur dioxide), so as to minimize the saccharide degradation and, consequently, the degradation of the overall production yield. These measures make it possible to produce pre-treated biomasses whose cellulose is highly accessible to the hydrolytic agents used in the saccharification process, while the degradation of the carbohydrates tends to take place at a reduced level.

The present invention includes examples of the treatment of various biomasses (i.e., defibered sugar cane and/or bagasse from the second three-roller milling combination), using catalytic systems (e.g., alkaline pre-treatment with ammonia or ammonium hydroxide), in addition to non-catalytic and autocatalytic processes using steam or water as chemical agents.

The products resulting from the treatment process can be used in various other processes, such as enzyme production, enzymatic hydrolysis, and fermentation, among others, in accordance with the various examples discussed hereinbelow.

Severity Level (S)

The level of severity of the treatment of the biomass according to the present invention is an index figure that reflects the pressure, temperature, and reaction time employed. For the purposes of the present invention, the severity level (S) is equivalent to Log $R_0$.

Enzyme Production

The process of obtaining enzymes includes the submerged or semi-solid culture, in fermenters, of a specific microorganism in substrates containing, for example, pre-treated sugar-cane bagasse. The pre-inoculation stage is performed using the stock in a solid medium in a test tube, in which the spores are suspended in a culture medium. A typical composition of a preferred culture medium consists of pre-treated biomass, a source of carbohydrates (e.g., saccharose, purified sugar-cane juice, or treated molasses), a source of plant protein (e.g., soy protein), and chemical adjuvants and nutrients, such as ammonium sulfate, urea, potassium phosphate, magnesium sulfate, calcium chloride, surfactants, antibiotics, and anti-foaming agents. The volume of inoculum may vary, depending on the characteristics of the available equipment and on the desired duration of the process.

The suspension of spores in culture medium is transferred, under completely aseptic conditions, from a test tube to the culture vials, and the culture vials are then transferred to an incubator table equipped with a shaking mechanism. The culture conditions typically include temperature ranging from 26° C. to 34° C., in processes implemented with mechanical shaking at a speed ranging from 80 rpm to 160 rpm, with aeration rates on the order of 6 vvm to 8 vvm, The process of enzyme production through fermentation requires a reaction time that is established in accordance with the enzyme formulation to be produced. In general, these processes require between 80 and 160 hours of operating time (i.e., loading, the reaction time, and unloading), also taking into consideration the intermediate operations consisting of checking and adjusting the pH, obtaining samples, and monitoring the aeration rate.

The Fermentative Process

The fermentation stage can be implemented after the enzymatic hydrolysis, by means of a process known as "SHF" (Separated Hydrolysis and Fermentation), or simultaneously with the hydrolysis, by means of a process known as "SSF" (Simultaneous Saccharification and Fermentation). Depending on the concentration of the sugars that are produced during the enzymatic hydrolysis, the decision may be made to add to the reaction medium a concentrated saccharide solution (e.g., molasses or sugar-cane juice), in a quantity ranging from 80 grams/liter to 820 grams/liter, and preferably between 120 grams/liter and 200 grams/liter.

The present invention also contemplates the possibility of the simultaneous implementation of the enzymatic pre-treatment of the hemicelluloses, the enzymatic hydrolysis of the cellulose, and the fermentation, through a consolidated bioprocess (GBP) that uses the treated biomass as a substrate.

A concentrated saccharide solution (known as a "booster"), which preferably consists of molasses or, optionally, sugar-cane juice, is preferably added to the fermenter at the start of the process or during the process, although the process can also be implemented without the addition of a saccharide solution. The sugar concentration of the saccharide booster solution ranges from 80 grams/liter to 820 grams/liter, and is preferably between 120 grams/liter and 200 grams/liter.

Example 1.—Production of Carbohydrates and Ethanol from Sugar-Cane Bagasse Produced by Means of a Non-Conventional Preparation (Using Chopped Sugar Cane or Bagasse from the First or Second Set of Rollers), Using the AFEX/AHFEX (Ammonia or Ammonium Hydroxide Fiber Explosion) Alkaline Catalytic Pre-Treatment, Enzymatic Hydrolysis, and Ethanolic Fermentation The alkaline AFEX/AHFEX pre-treatment operation consists of loading the biomass (without any prior treatment, such as washing, milling, or granular metrics operation) [into a reactor]. After loading of the discontinuous reactor and during the heating process, the impregnation of the biomass with a chemical agent (i.e., ammonia or ammonium hydroxide) is begun. After the operational pressure and temperature (7.0 to 15.0 kgf/cm$^2$ and 90° C. to 160° C.) have been reached, the reaction takes place, with the mixture being left to "cook" during the operational period (ranging from 10 minutes to 120 minutes). Then the discharge valve located at the base of the reactor is opened (either suddenly or in a controlled manner) so as to cause the decompression of the reactor, with the expulsion of the mass into a cyclone system or a tank for the collection of the pre-treated material.

Table 1 shows the results of an integrated process for the production of carbohydrates, first-generation ethanol, and second-generation ethanol from chopped sugar cane and bagasse, pre-treated via AFEX/AHFEX and output by the second set of three-roller milling combinations. The Simultaneous Saccharification and Fermentation (SSF) technique was used, with cellulolytic enzymes (i.e., cellulases), β-glucosidases, and hemicellulases, with a view toward the production of carbohydrates (e.g., glucose and xylose) from the bagasse or from the chopped sugar cane. In some cases, molasses was incorporated as a source of total reducing sugars (i.e., implementation of the "boosting" technique), in order to promote the reaction consisting of the biochemical conversion of the carbohydrates and ethanol.

the mixture being left to "cook" during the reaction time (ranging from 2 minutes to 20 minutes). Then the discharge valve of the reactor is opened, so as to cause the sudden decompression of the reactor, with the expulsion of the mass into a cyclone system or a tank in which the pre-treated material is collected.

For steam-based pre-treatment processes in catalytic and non-catalytic systems, the time required to reach the working pressure may contribute significantly to the severity of the process. Furthermore, the pressurization ramp-up, and consequently the temperature profile, may also be treated as a process variable that has a significant impact on the characteristics of the pre-treated biomass. The need to investigate different pressurization and heating profiles under different levels of severity requires an integrative

TABLE 1

|  | A | B | C | D | E | F |
|---|---|---|---|---|---|---|
| Source of the sugars | Fiber only | Fiber only | Fiber/ molasses | Fiber/ molasses | Molasses only | Molasses only |
| Type of fermentation | SSF | SSF | SSF | SSF | Conv. | Conv. |
| Pre-treated wet biomass (g) | 129.1 | 129.1 | 129.1 | 129.3 | 0.0 | 0.0 |
| Solids load (%) | 1.0 | 1.0 | 0.7 | 0.7 | 0.0 | 0.0 |
| Juice or molasses load (g) | 0.0 | 0.0 | 376.7 | 376.5 | 113.0 | 113.0 |
| Cellulase (grams per 100 g of biomass) | 10.8 | 10.8 | 10.8 | 10.8 | 0.0 | 0.0 |
| β-glucosidase (grams per 100 g of biomass) | 2.5 | 2.5 | 2.5 | 2.5 | 0.0 | 0.0 |
| Hemicellulase (grams per 100 g of biomass) | 0.9 | 0.9 | 0.9 | 0.9 | 0.0 | 0.0 |
| Inoculum (g) | 26.9 | 26.9 | 38.6 | 38.6 | 5.0 | 5.0 |
| Total sugar conc. (%) | 1.6 | 1.6 | 10.0 | 9.9 | 12.0 | 12.0 |
| Sugars in the juice or molasses (g) | 0.0 | 0.0 | 119.9 | 119.9 | 36.0 | 36.0 |
| Sugars in the fiber (g) | 15.9 | 15.9 | 15.9 | 15.9 | 0.0 | 0.0 |
| Cellulose conv. (%) | 100 | 100 | 100 | 100 | N/A | N/A |
| Dry yeast base (g) | 9.0 | 9.0 | 13.0 | 13.0 | 2.0 | 2.0 |
| Type of ethanol | 2G | 2G | 1G/2G | 1G/2G | 1G | 1G |
| Fermentative yield (%) | 53.3 | 57.9 | 77.2 | 76.7 | 71.6 | 69.9 |

1G: First-generation ethanol.
2G: Second-generation ethanol.
SSF: Simultaneous Saccharification and Fermentation.
Conv.: Conventional.

Figure 9:
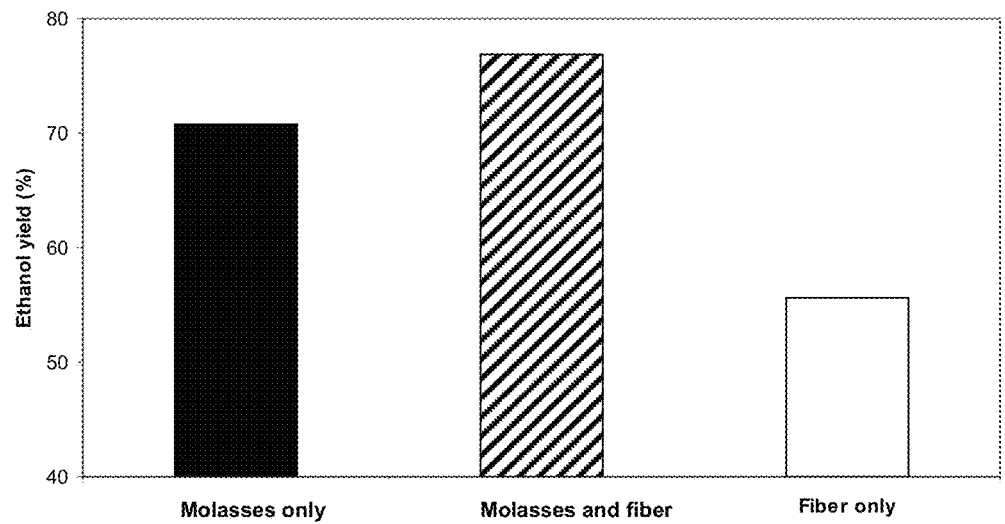
FIG. 9 illustrates the ethanol yield for different enzymatic hydrolysate combinations.

As can be seen in FIG. 9, the combination of enzymatic hydrolysis and molasses tends to favor the performance of the microorganism (*Saccharomices cerevisae*) used in the fermentative process, reflecting a positive synergy between the first-generation ethanol process (which uses only molasses) and the second-generation ethanol process (which uses only fiber).

Figure 10:
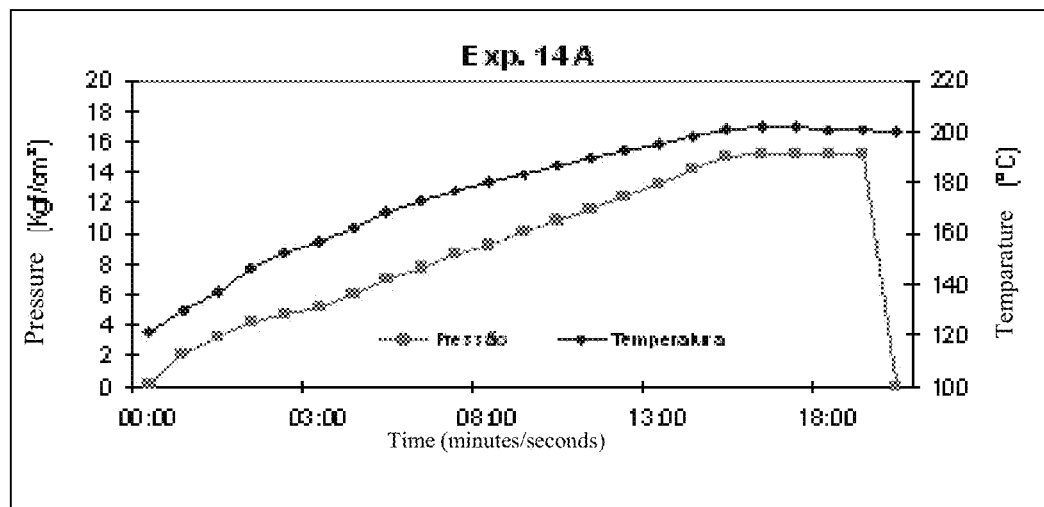
FIG. 10 shows Typical Profile No. 1, with a gentle ramp-up and sudden decompression.
Figure 11:
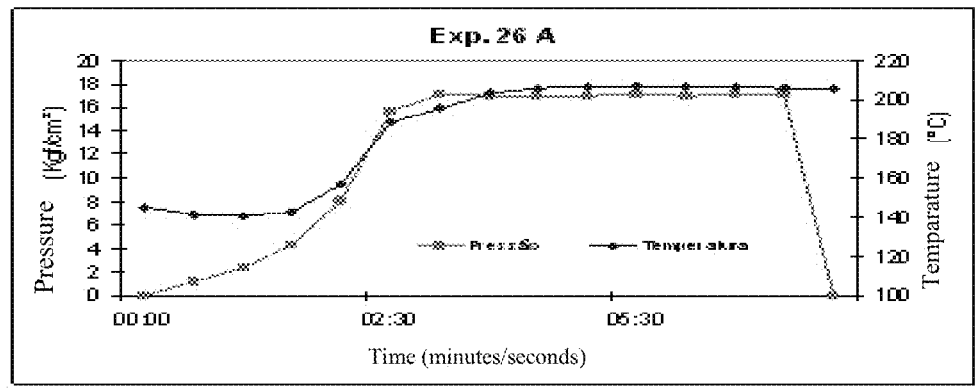
FIG. 11 shows Typical Profile No. 2, with an intense ramp-up and sudden decompression.
Figure 12:
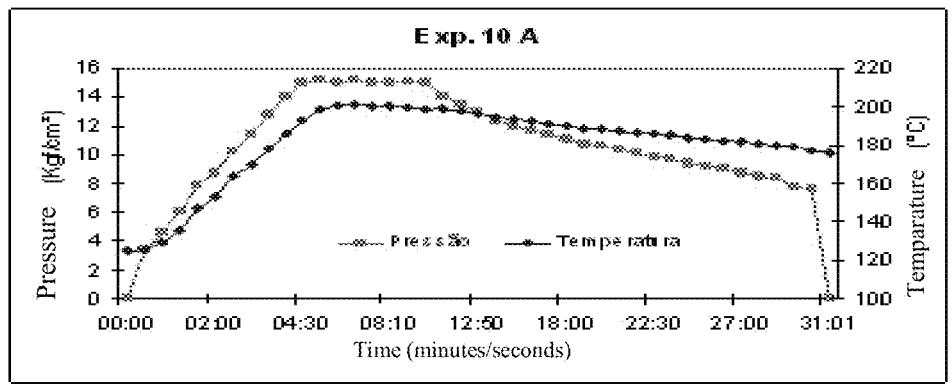
FIG. 12 shows Typical Profile No. 3, with an intermediate ramp-up and gentle decompression.
Figure 13:
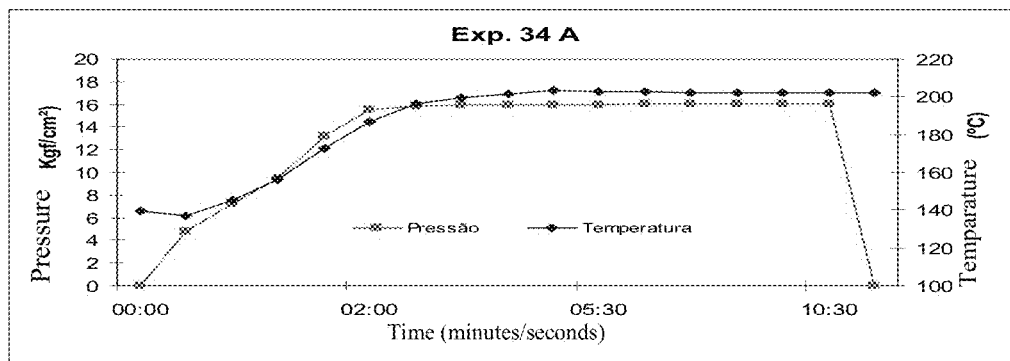
FIG. 13 shows Typical Profile No. 4, with an intermediate ramp-up and sudden decompression.
Figure 14:
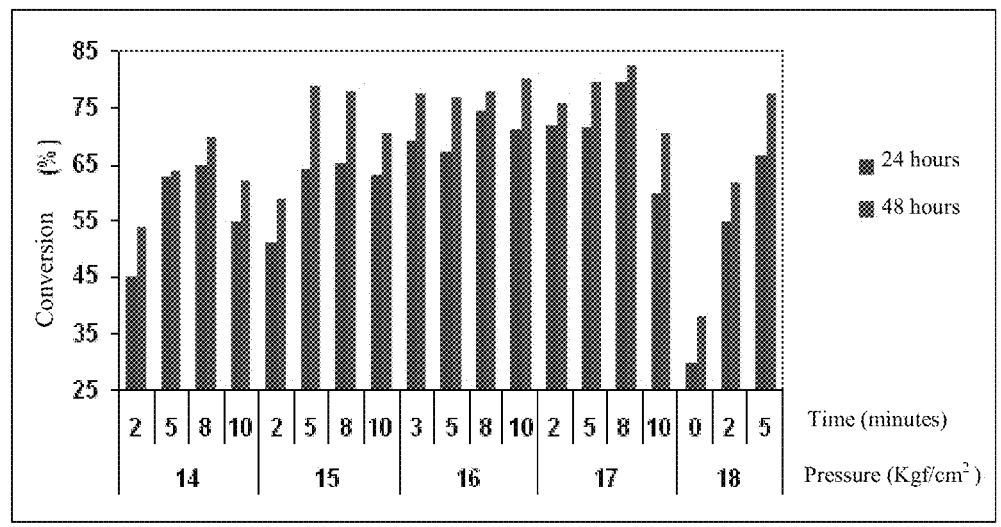
FIG. 14 shows the conversions obtained in the tests of the enzymatic reactivity of the pre-treated bagasses at different severity levels, with a gentle ramp-up and sudden decompression.
Figure 15:
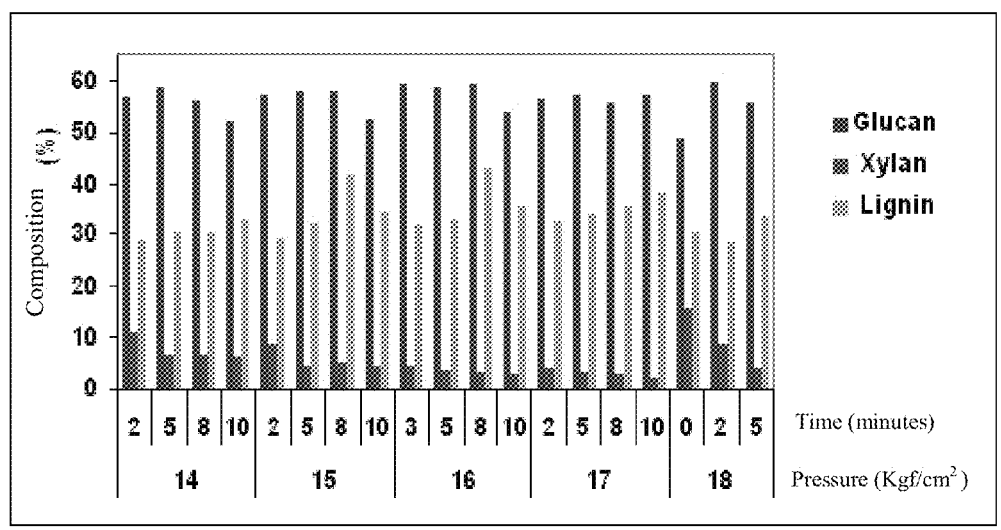
FIG. 15 shows the composition of the pre-treated bagasse under different operating conditions, with a gentle ramp-up and sudden decompression.
Figure 16:
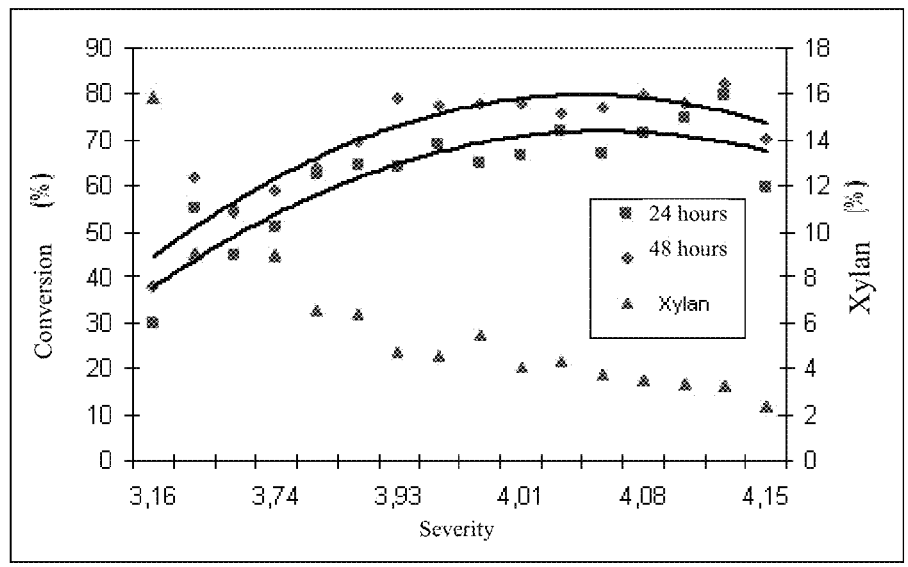
FIG. 16 shows the percentage of xylans in relation to the conversions obtained in the tests of the enzymatic reactivity of the pre-treated bagasses at different severity levels and under different operating conditions, with a gentle ramp-up and sudden decompression.
Figure 17:
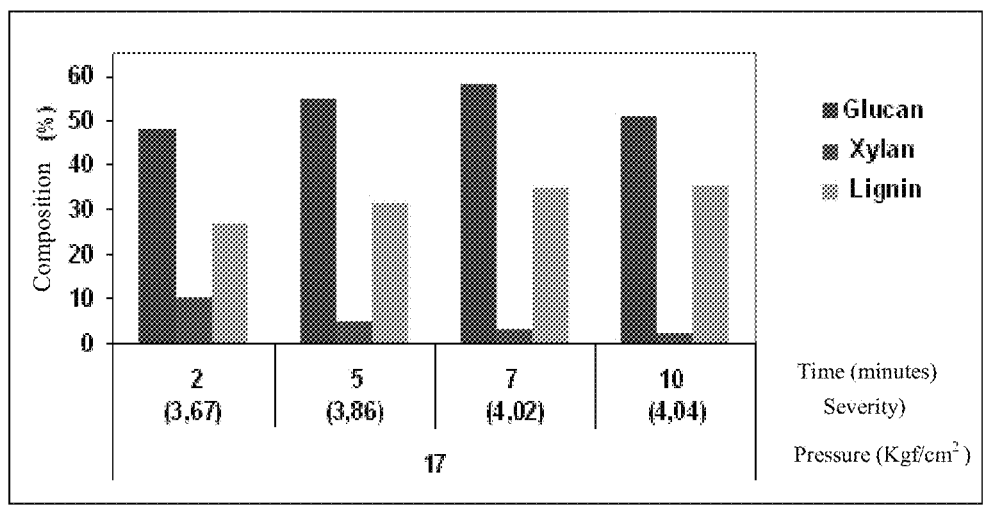
FIG. 17 shows the composition of the pre-treated bagasse at different severity levels and under different operating conditions, with an intense ramp-up and sudden decompression.
Figure 18:
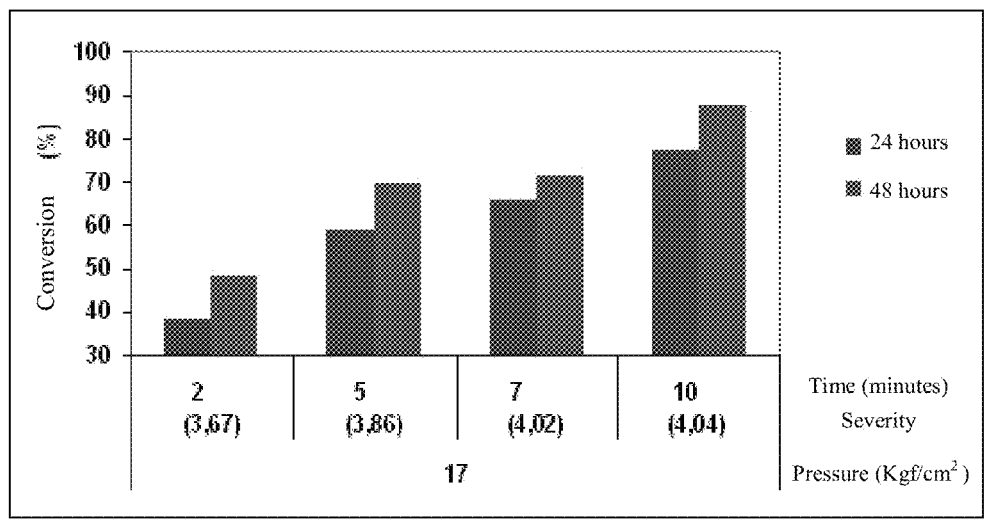
FIG. 18 shows the enzymatic conversions of the pre-treated bagasses at different severity levels, with an intense ramp-up and sudden decompression.
Figure 19:
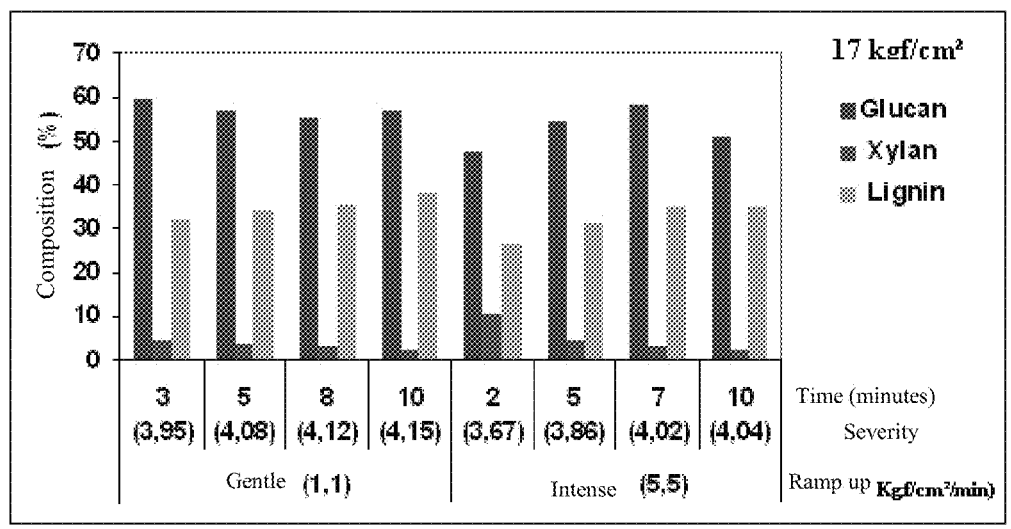
FIG. 19 shows the composition of the bagasses that were pre-treated with steam, as produced at different severity levels and with different heating ramp-ups (both gentle and intense), with sudden decompression.
Figure 20:
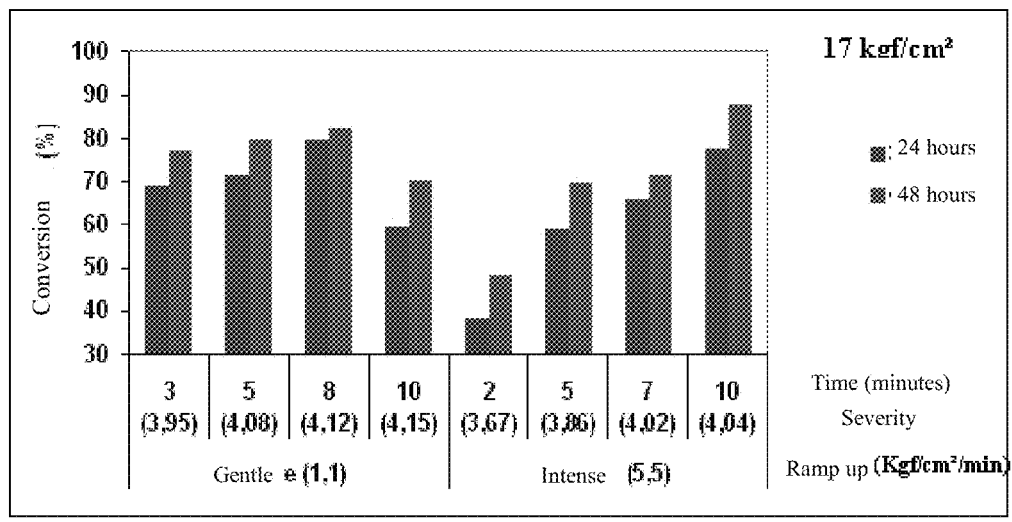
FIG. 20 shows the enzymatic conversions of the cellulose in the bagasses that were pre-treated with steam, at different severity levels and with different heating ramp-ups (both gentle and intense), with sudden decompression.
Figure 21:
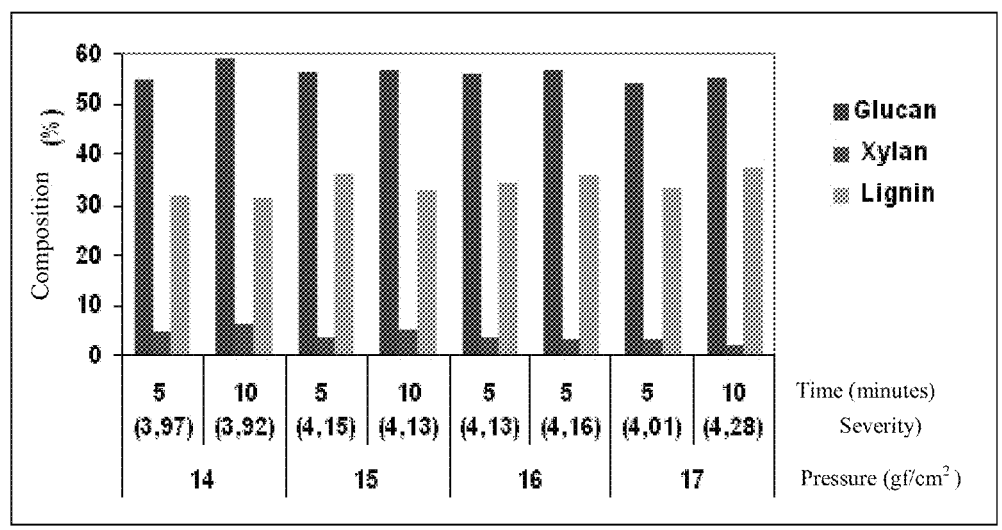
FIG. 21 shows the composition of the pre-treated bagasse at different severity levels and under different operating conditions, with an intermediate ramp-up and gentle decompression.
Figure 22:
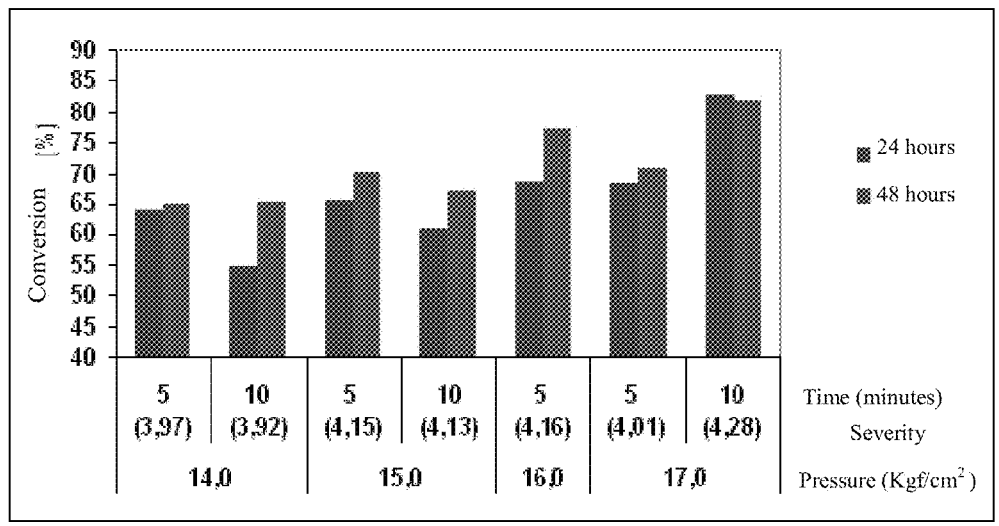
FIG. 22 shows the enzymatic conversions of the pre-treated bagasses at different severity levels, with an intermediate ramp-up and gentle decompression.
Figure 23:
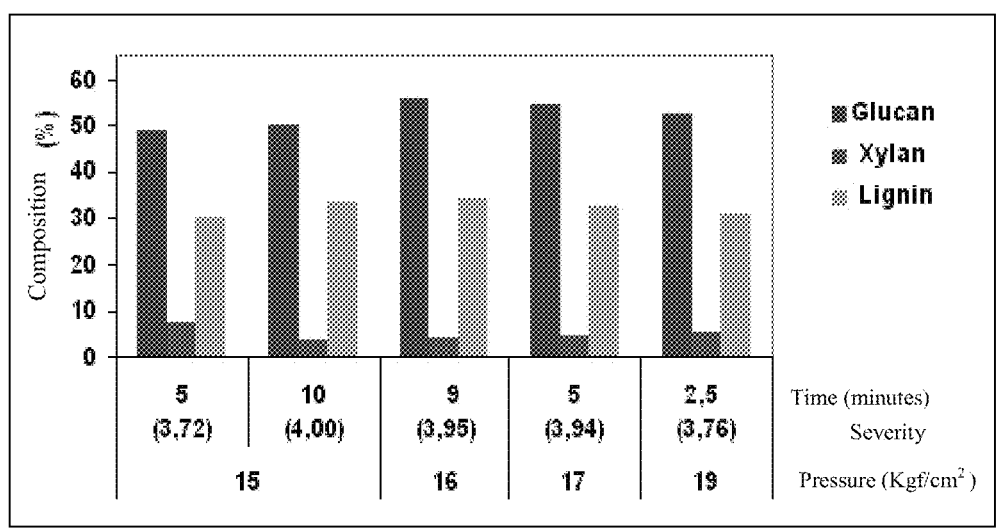
FIG. 23 shows the composition of the pre-treated bagasse at different severity levels and under different operating conditions, with an intermediate ramp-up, sudden decompression, and head space of 50%.
Figure 24:
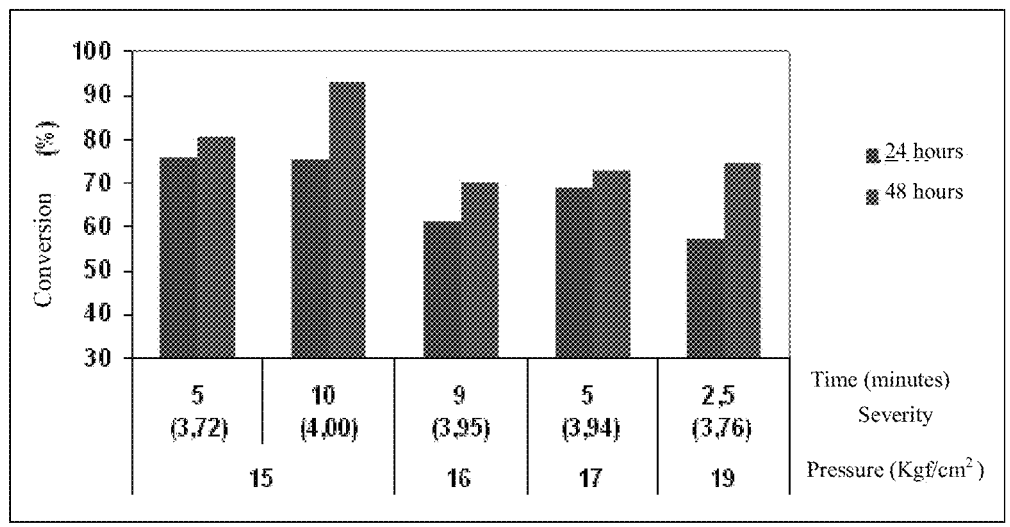
FIG. 24 shows the enzymatic conversions of the pre-treated bagasses at different severity levels and under different operating conditions, with a typical profile consisting of an intermediate ramp-up, sudden decompression, and head space of 50%.

Example 2.—Production of Carbohydrates from Sugar-Cane Bagasse Produced Through Conventional Milling Using STEX (Steam Explosion) Pre-Treatment in Non-Catalytic Systems The steam-based pre-treatment operation consists initially of loading the biomass (without any prior treatment, such as washing, milling, or granular metrics operation) [into a reactor]. After the discontinuous reactor is loaded, heating is begun through the injection of saturated steam (20 to 23 kgf/cm²) in direct contact with the biomass present in the reactor (see the typical operating profile shown in FIG. 10, so as to reach the operational pressure and temperature (12.0 to 20.0 kgf/cm² and 160° C. to 220° C.), using an appropriate heating ramp-up. The reaction per se then takes place, with approach to the severities for each time interval within an average temperature range, in accordance with the following equation:

$$R_0 = \int_{t1}^{t2} \exp\left(\frac{T - 100}{14.75}\right) dt. \qquad \text{Equation (1)}$$

where $t_1$ and $t_2$ refer to the starting and ending times of the interval, expressed in minutes, for an average temperature T for the process interval, which temperature is expressed in ° C.

The following examples refer to the steam-based pre-treatment processes that use sugar-cane bagasse produced by means of conventional milling, containing approximately 39% cellulose (37% to 41%), 22% xylans (18% to 26%), and 23% lignin that is insoluble in acid (17% to 26%). The processes were implemented under levels of severity (Log $R_0$) ranging between 3.16 and 4.28 (14.0 to 18.5 kgf/cm², and 0 to 10 minutes), in non-catalytic or autocatalytic systems, using the water contained in the original bagasse. Different pressurization profiles, and consequently different reactor heating profiles were investigated, which included a gentle ramp-up (1.1±0.5 kgf/cm²/minute), an intermediate ramp-up (2.8±0.5 kgf/cm²/minute), and an intense ramp-up (5.5±1.0 kgf/cm²/minute), and gentle and sudden decompressions applied at pressures on the order of 11.0±1.0 kgf/cm² and at the threshold pressure, respectively. An attempt was also made to investigate the effect of the reactor load—including, in particular the equipment occupancy level (with head space of 0% and 50%)—on the properties of the pre-treated bagasse. Table 2 shows the properties of the four typical profiles that were investigated, taking into consideration the type of ramp-up and decompression. Typical profiles can be seen in FIGS. 10 through 24. The operational variables and the severity of the process for each of the experiments that was conducted are shown in tables 3 through 6, which group together the experiments that were conducted for each of the typical profiles.

TABLE 2

Typical profiles containing the type of ramp-up and decompression.

| Typical profile | Ramp-up | Decompression |
|---|---|---|
| 1 | Gentle (1.1 ± 0.5 kgf/cm²/min.) | Sudden |
| 2 | Intense (5.5 ± 1.0 kgf/cm²/min.) | Sudden |
| 3 | Intermediate (2.8 ± 0.5 kgf/cm²/min.) | Gentle |
| 4 | Intermediate (2.8 ± 0.5 kgf/cm²/min.) | Sudden |

The bagasse pre-treatment processes produce substrates with high cellulose contents and a high level of enzymatic reactivity under different process conditions, including reduced pressures on the order of 14 kgf/cm². Maximum reactivity was displayed for pressure levels of 17 kgf/cm² and a reaction time of 10 minutes, reflecting severities of nearly 4.30. It was observed that at this level of severity, a pre-treated bagasse was produced that had a lower xylan content and a higher glycan content. The intense and selective removal of the xylans tends to produce substrates with a high level of enzyme accessibility to the cellulosic matrix, resulting in elevated conversions into glucose. It was observed that the use of very severe conditions tends to increase the solubilization of the cellulose and the subsequent removal of the glycans to the liquid phase, in the form of glucose and degradation products, thereby impairing the overall productive yield.

The following tables show the compositions of the bagasses that were pre-treated with steam, as produced under different process profiles in non-catalytic (or autocatalytic) systems. The yields of the processes for the production of carbohydrates by means of enzymatic hydrolysis (expressed in terms of conversion of cellulose into glucose), as performed on the various pre-treated bagasses using formulations of cellulases and β-glucosidase, are shown separately.

TABLE 3

Compositions, soluble solids, and yield of the enzymatic hydrolysis of the pre-treated bagasses, under different process operating conditions and severities, for experiments with a gentle ramp-up (1.1 ± 0.5 kgf/cm²/minute) and sudden decompression. The head space was 0 (zero), and the solids load in the reactor was 71 kg/m³.

| | | | | Composition of the pre-treated bagasse (%) | | | Yield of the enzymatic hydrolysis process (%) | |
|---|---|---|---|---|---|---|---|---|
| P (atm) | t (min.) | T (° C.) | S | Glycan | Xylan | Lignin | 24 hours | 48 hours |
| 14.0 | 2 | 199 | 3.71 | 56.80 | 11.16 | 29.01 | 45.14 | 53.94 |
| 14.0 | 5 | 198 | 3.84 | 58.86 | 6.54 | 30.49 | 62.65 | 63.66 |
| 14.0 | 8 | 197 | 3.92 | 56.17 | 6.40 | 30.50 | 64.80 | 69.69 |
| 14.0 | 10 | 198 | 3.91 | 52.31 | 6.38 | 33.40 | 55.15 | 62.55 |
| 15.0 | 2 | 198 | 3.74 | 57.43 | 8.99 | 29.23 | 51.24 | 58.86 |
| 15.0 | 5 | 201 | 3.93 | 58.04 | 4.77 | 32.65 | 64.03 | 78.84 |
| 15.0 | 8 | 200 | 3.99 | 58.03 | 5.51 | 41.83 | 65.14 | 77.82 |
| 15.0 | 10 | 201 | 3.99 | 52.79 | 4.80 | 34.31 | 63.10 | 70.57 |
| 16.0 | 3 | 201 | 3.95 | 59.72 | 4.57 | 32.16 | 69.15 | 77.50 |
| 16.0 | 5 | 204 | 4.06 | 58.67 | 3.73 | 33.44 | 67.19 | 76.77 |
| 16.0 | 8 | 202 | 4.09 | 59.60 | 3.34 | 42.79 | 74.93 | 77.96 |
| 16.0 | 10 | 201 | 4.02 | 53.98 | 3.22 | 35.74 | 71.36 | 80.25 |
| 17.0 | 2 | 205 | 4.03 | 56.56 | 4.36 | 33.00 | 71.88 | 75.88 |
| 17.0 | 5 | 205 | 4.08 | 57.43 | 3.50 | 34.05 | 71.55 | 79.70 |
| 17.0 | 8 | 202 | 4.12 | 55.54 | 3.24 | 35.46 | 79.72 | 82.43 |
| 17.0 | 10 | 206 | 4.15 | 57.41 | 2.37 | 38.27 | 59.77 | 70.39 |
| 18.5 | 0 | 205 | 3.16 | 48.66 | 15.85 | 30.73 | 30.01 | 38.14 |
| 18.5 | 2.5 | 207 | 3.69 | 59.97 | 9.04 | 28.79 | 55.11 | 61.90 |
| 18.5 | 5 | 209 | 4.01 | 55.57 | 4.07 | 33.80 | 66.75 | 77.57 |

Yield of the enzymatic hydrolysis process, expressed in terms of the conversion of cellulose into glucose.

TABLE 4

Compositions, soluble solids, and yield of the enzymatic hydrolysis of the pre-treated bagasses, under different process operating conditions and severities, for experiments with an intense ramp-up (5.5 ± 1.0 kgf/cm²/minute) and sudden decompression. Head space: 0 (zero). Solids load: 71 kg/m³ in the reactor.

| | | | | Composition of the pre-treated bagasse (%) | | | Yield of the enzymatic hydrolysis process (%) | |
|---|---|---|---|---|---|---|---|---|
| P (atm) | T (min.) | T (° C.) | S | Glycan | Xylan | Lignin | 24 hours | 48 hours |
| 17.0 | 2 | 205 | 3.67 | 47.64 | 10.39 | 26.57 | 38.51 | 48.07 |
| 17.0 | 5 | 206 | 3.86 | 54.60 | 4.58 | 31.52 | 58.94 | 69.91 |
| 17.0 | 7 | 204 | 4.02 | 58.06 | 3.15 | 34.81 | 65.83 | 71.44 |
| 17.0 | 10 | 202 | 4.04 | 50.87 | 2.27 | 35.17 | 77.60 | 87.54 |

TABLE 5

Compositions, soluble solids, and yield of the enzymatic hydrolysis of the pre-treated bagasses, under different process operating conditions and severities, for experiments with an intermediate ramp-up (2.8 ± 0.5 kgf/cm²/minute) and gentle decompression (11.0 ± 1.0 kgf/cm²). Head space: 0 (zero). Solids load: 71 kg/m³ in the reactor.

| | | | | Composition of the pre-treated bagasse (%) | | | Yield of the enzymatic hydrolysis process (%) | |
|---|---|---|---|---|---|---|---|---|
| P (atm) | T (min.) | T (° C.) | S | Glycan | Xylan | Lignin | 24 hours | 48 hours |
| 14.0 | 5 | 199 | 3.97 | 55.33 | 4.84 | 31.92 | 64.09 | 65.09 |
| 14.0 | 10 | 194 | 3.92 | 59.10 | 6.27 | 31.52 | 54.95 | 65.17 |
| 15.0 | 5 | 200 | 4.15 | 56.40 | 3.41 | 36.16 | 65.81 | 70.25 |
| 15.0 | 10 | 200 | 4.13 | 56.67 | 4.99 | 32.98 | 61.23 | 67.20 |
| 16.0 | 5 | 202 | 4.16 | 56.63 | 3.33 | 35.70 | 68.74 | 77.18 |
| 17.0 | 5 | 203 | 4.01 | 54.26 | 3.35 | 33.30 | 68.58 | 70.94 |
| 17.0 | 10 | 203 | 4.28 | 55.49 | 2.08 | 37.53 | 82.99 | 81.98 |

TABLE 6

Compositions, soluble solids, and yield of the enzymatic hydrolysis of the pre-treated bagasses, under different process operating conditions and severities, for experiments with an intermediate ramp-up (2.8 ± 1.0 [sic] kgf/cm²/minute) and sudden decompression. Head space: 50%. Solids load: 46 kg/m³ in the reactor.

| | | | | Composition of the pre-treated bagasse (%) | | | Yield of the enzymatic hydrolysis process (%) | |
|---|---|---|---|---|---|---|---|---|
| P (atm) | T (min.) | T (° C.) | S | Glycan | Xylan | Lignin | 24 hours | 48 hours |
| 15.0 | 5 | 200 | 3.72 | 48.93 | 7.37 | 30.12 | 75.84 | 80.54 |
| 15.0 | 10 | 200 | 4.00 | 50.19 | 3.98 | 33.55 | 75.41 | 93.40 |
| 17.0 | 5 | 206 | 3.94 | 54.84 | 4.83 | 32.78 | 68.89 | 72.63 |
| 18.5 | 2.5 | 208 | 3.76 | 52.7 | 5.8 | 31.1 | 57.38 | 74.66 |

Example 3.—Production of Carbohydrates from Sugar-Cane Bagasse Produced Through Conventional Milling Using STEX (Steam Explosion) Pre-Treatment in Autocatalytic Systems Tables 7 and 8 show the composition of the bagasse that was pre-treated with steam in systems that were auto-catalyzed with acetic acid obtained from the deacetylation of the hemicelluloses (xylans). As can be seen, the said bagasse displayed a significantly higher glycan content and a significantly lower xylan content than had been detected in the original biomass. This change is due essentially to the intense and selective removal of the hemicelluloses during the process, as also indicated by the acidity of the resulting biomass (with a pH within the range from 3 to 4), as well as by the higher xylose content and the reduced glucose content of the soluble solids. As can be seen, there is a clear predominance of non-saccharide compounds among the soluble solids, indicating the likely conversion of carbohydrates (particularly xylose and arabinose) and of lignin into chemical species such as organic acids (e.g., acetic acid) and phenolic compounds. In summary, it is clear that the pre-treatment of the bagasse, as performed under the operational conditions described here, is characterized by elevated productive efficiency, based on the elevated, intense, and selective extraction of hemicelluloses, with a reduced cellulosic loss in the fiber.

TABLE 7

Composition of the pre-treated bagasse.

| Constituent | % |
|---|---|
| Humidity | 58.3 |
| Total solids | 41.7 |
| Insoluble solids (fiber) | 79.3 |
| Glycans | 55.4 |
| Xylans | 3.2 |
| Lignin | 35.4 |
| Other insoluble solids | 6.0 |
| Soluble solids (SS) | 20.7 |
| Glucose | 3.8 |
| Xylose | 14.5 |
| Arabinose | 0.8 |
| Other soluble solids | 80.9 |

Figure 25:
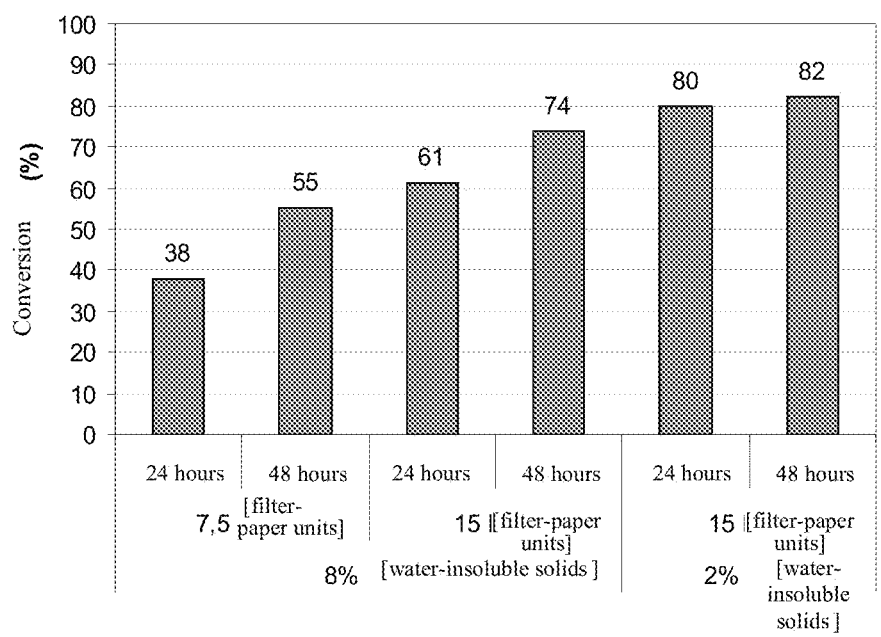
FIG. 25 shows the conversions of the cellulose into glucose under different process conditions (enzymatic hydrolysis of the bagasse that was pre-treated with steam).

Table 8 and FIG. 25 show the conversions of the cellulose into glucose, as obtained through the hydrolysis of the pre-treated bagasse with different enzyme loads, processing times, and solids loads, using cellulose and β-glucosidase.

TABLE 8

Enzymatic hydrolysis of the bagasse pre-treated with steam.

| Condition | Solids load (%) | Cellulase load (FPU*/g of fiber) | Hydrolysis time (hours) | Cellulose conversion (%) |
|---|---|---|---|---|
| 1 | 8 | 7.5 | 24 | 38 |
| 2 | 8 | 7.5 | 48 | 55 |
| 3 | 8 | 15.0 | 24 | 61 |
| 4 | 8 | 15.0 | 48 | 74 |
| 5 | 2 | 15.0 | 24 | 80 |
| 6 | 2 | 15.0 | 48 | 82 |

Conversion of cellulose into glucose.
*[FPU = Filter-paper unit.]

Example 4.—Production of Carbohydrates from Sugar-Cane Bagasse Using the WEX (Wet Explosion or Water Explosion) Pre-Treatment in Catalytic and Non-Catalytic (Autocatalytic) Systems The WEX (Water Explosion or Wet Explosion) pre-treatment operation initially consists of loading the reactor with the biomass along with the reagents. Unlike the STEX process, in the WEX process heating is done without an injection of steam into the biomass. In this system, part of the water present in the reaction medium is vaporized, thereby producing "in camera" steam during the period in which the operational pressure and temperature are reached by means of an appropriate heating ramp-up. Next, the reaction per se takes place, with the mixture being left to "cook" during the reaction time. The reactor is then emptied by means of the opening of the valve, which causes the sudden decompression of the equipment and the resulting discharge of the pre-treated biomass into a collection tank.

For WEX pre-treatment processes in catalytic and non-catalytic systems, the time required to reach the working temperature affects the overall severity of the process, with an impact on the properties of the pre-treated biomass. Different pressurization and heating profiles under different levels of severity can be integrated for each time interval within an average temperature range, in accordance with the following equation, which characterizes the severity of the process:

$$R_0 = \int_{t1}^{t2} \exp\left(\frac{T-100}{14.75}\right) dt. \qquad \text{Equation (1)}$$

where $t_1$ and $t_2$ refer to the starting and ending times of the interval, expressed in minutes, for an average temperature T for the process interval, which temperature is expressed in °C.

Figure 26:
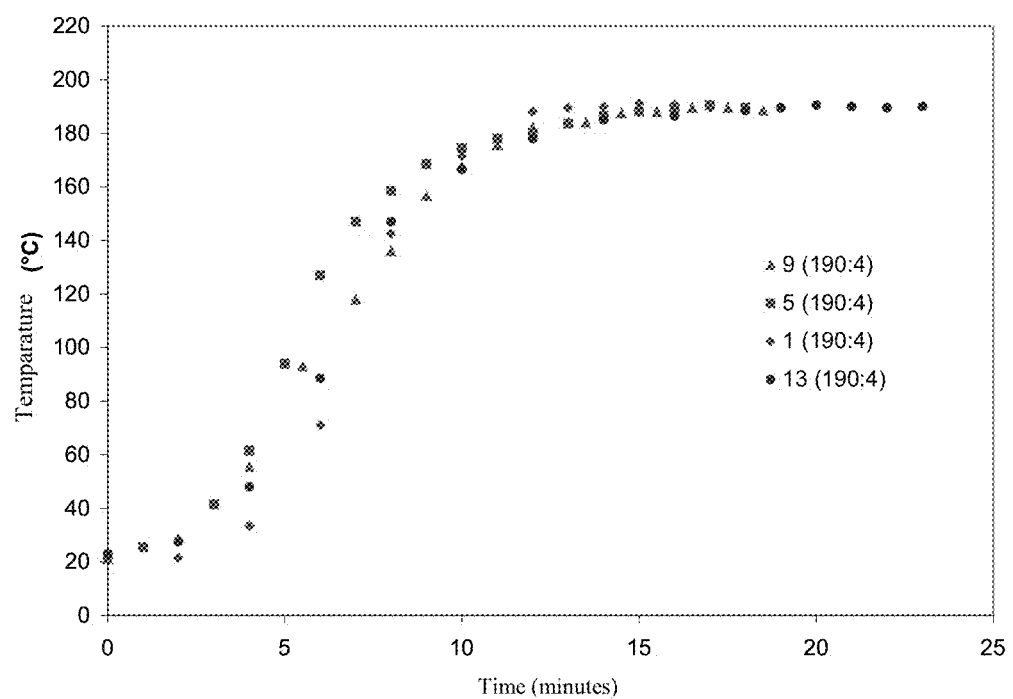
FIG. 26 shows the typical profile for the WEX process, as conducted at a temperature of 190° C. for a period of 4 minutes.

The following examples refer to the WEX pre-treatment processes that use sugar-cane bagasse produced by means of conventional milling, containing approximately 39% cellulose (37% to 41%), 22% xylans (18% to 26%), and 23% lignin that is insoluble in acid (17% to 26%). The processes were conducted in non-catalytic or autocatalytic systems, using the water contained in the original bagasse itself. Different operating conditions of temperature (190° C. to 210° C.), reaction time (4 to 12 minutes), catalyst load (0 to 1.6 g per 100 g), hydromodule or liquid-to-solid ratio (10 to 20) and head space (0% or 50%) were used in typical profiles, as indicated in Table 9 and in FIG. 26.

TABLE 9

Experimental conditions used in certain catalytic and non-catalytic WEX processes.

| No. | Temperature (° C.) | Time (min.) | $H_3PO_4$ conc. (g/100 g BS) | Hydro-module (L/S) | Head space (%) |
|---|---|---|---|---|---|
| 1 | 190 | 4 | 0 | 10 | 50 |
| 2 | 210 | 4 | 0 | 10 | 0 |
| 3 | 190 | 12 | 0 | 10 | 0 |
| 4 | 210 | 12 | 0 | 10 | 50 |
| 5 | 190 | 4 | 1 | 10 | 0 |
| 6 | 210 | 4 | 1 | 10 | 50 |
| 7 | 190 | 12 | 1 | 10 | 50 |
| 8 | 210 | 12 | 1 | 10 | 0 |
| 9 | 190 | 4 | 0 | 20 | 50 |
| 10 | 210 | 4 | 0 | 20 | 0 |
| 11 | 190 | 12 | 0 | 20 | 0 |
| 12 | 210 | 12 | 0 | 20 | 50 |
| 13 | 190 | 4 | 1 | 20 | 0 |
| 14 | 210 | 4 | 1 | 20 | 50 |
| 15 | 190 | 12 | 1 | 20 | 50 |
| 16 | 210 | 12 | 1 | 20 | 0 |
| 17 | 200 | 8 | 0.5 | 15 | 25 |
| 18 | 200 | 8 | 0.5 | 15 | 25 |
| 19 | 200 | 8 | 0.5 | 15 | 25 |
| 20 | 200 | 8 | 0.5 | 15 | 25 |

Figure 27:
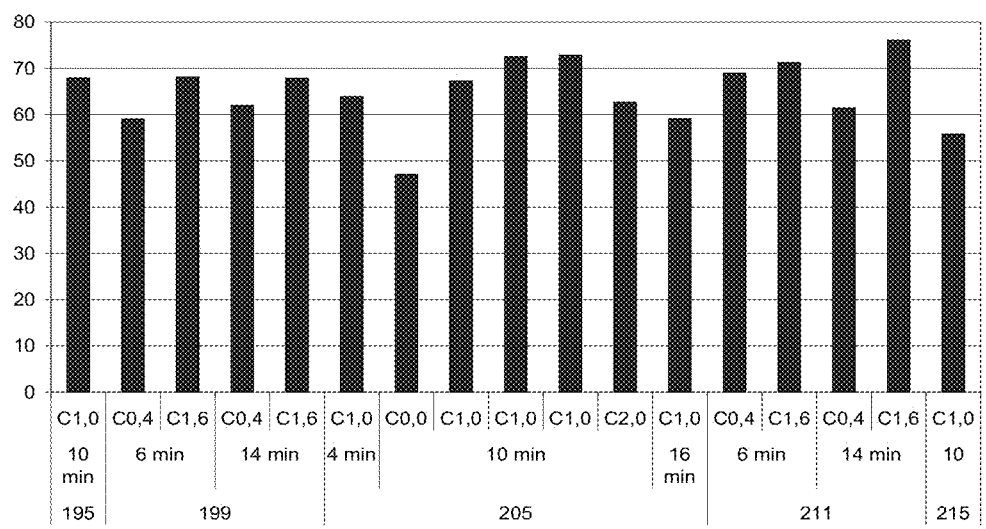
FIG. 27 shows the enzymatic hydrolysis yield of the bagasse that was pre-treated using the WEX process (both catalytic and non-catalytic) under different temperature conditions (195° C. to 215° C.), reaction times (4 to 16 minutes), and catalyst loads (0 to 1.6 grams per 100 grams of dry bagasse). The values are expressed in terms of the conversion of cellulose into glucose.

Table 10 and FIG. 27 show the principal productive and operating parameters of the WEX process (catalytic and non-catalytic) for the pre-treatment of the bagasse. Among these parameters, "H" refers to the hydromodule (i.e., the liquid-to-solid ratio); "HS" refers to the head space; and "C" refers to the catalytic load that was employed.

TABLE 10

Productive and operating parameters of the WEX process (catalytic and non-catalytic) for the pre-treatment of the bagasse.

| Temp. (° C.) | Time (min.) | Catalytic load (g/100 g BS) | Head space (%) | Hydromodule (L/S) | Recovered fiber (%) | Recovered soluble solids (%) | Losses (%) |
|---|---|---|---|---|---|---|---|
| 190 | 4 | 0 | 50 | 10 | 64 | 14 | 21 |
|  |  |  |  | 20 | 83 | 10 | 7 |
|  |  | 1 | 0 | 10 | 72 | 15 | 12 |
|  |  |  |  | 20 | 62 | 12 | 25 |
|  | 12 | 0 | 0 | 10 | 59 | 13 | 28 |
|  |  |  |  | 20 | 67 | 11 | 21 |
|  |  | 1 | 50 | 10 | 62 | 12 | 25 |
|  |  |  |  | 20 | 65 | 13 | 22 |
| 200 | 8 | 0.5 | 25 | 15 | 50 | 11 | 39 |
|  |  |  |  | 15 | 65 | 10 | 25 |
|  |  |  |  | 15 | 54 | 12 | 34 |
|  |  |  |  | 15 | 58 | 8 | 34 |
| 210 | 4 | 0 | 0 | 10 | 59 | 15 | 26 |
|  |  |  |  | 20 | 48 | 10 | 42 |
|  |  | 1 | 50 | 10 | 58 | 9 | 33 |
|  |  |  |  | 20 | 74 | 10 | 16 |
|  | 12 | 0 | 50 | 10 | 56 | 6 | 38 |
|  |  |  |  | 20 | 52 | 9 | 40 |
|  |  | 1 | 0 | 10 | 57 | 5 | 38 |
|  |  |  |  | 20 | 49 | 9 | 42 |

H: Hydromodule.
HS: Head space.
C: Catalytic load.

The invention claimed is:

1. A process for the treatment of sugar cane biomass, consisting of the stages of:
   a) defibrating the sugar cane biomass;
   b) milling the defibrated sugar cane biomass, the milling stage characterized by at most 3 three-roller milling combinations, resulting in a saccharose content primary juice, and a bagasse containing a residual amount of saccharose and a fibrous fraction;
   c) separating the saccharose content primary juice of stage b) from the bagasse of stage b); and then
   d) submitting the bagasse obtained in stage c) to a one-step physico-chemical treatment with addition of at least one chemical agent at conditions with severity level (S) within the range from 3.70 to 4.50
   wherein the at least one chemical agent added is selected from the group consisting of ammonia, ammonium hydroxide, water steam, water, and combinations thereof.

2. The process according to claim 1, wherein the defibrating stage includes the placement of the sugar cane biomass in a piece of equipment selected from the group consisting of a blade mill and a knife mill.

3. The process according to claim 1, wherein the milling stage includes the use of 2 three roller milling combinations.

4. The process according to claim 1, wherein stage d) is a non-catalytic or auto-catalytic process.

5. The process according to claim 1, wherein the one-step physico-chemical treatment is an AFEX alkaline catalytic treatment.

6. The process according to claim 1, wherein the one-step physico-chemical treatment is an AHFEX alkaline catalytic treatment.

7. The process according to claim 4, wherein the one-step physico-chemical treatment is a STEX treatment.

8. The process according to claim 4, wherein the one-step physico-chemical treatment is a WEX treatment.

9. An integrated process for the production of cellulosic ethanol from a sugar cane biomass, consisting of the stages of:
   a) defibrating a sugar cane biomass;
   b) milling the defibrated sugar cane biomass, the milling stage characterized by at most 3 three-roller milling combinations, resulting in a saccharose content primary juice and a bagasse containing a residual amount of saccharose and a fibrous fraction;
   c) submitting the bagasse obtained in stage b) to a one-step physico-chemical treatment with addition of at least one chemical agent at conditions with severity level (S) is within the range from 3.70 to 4.50;
   d) hydrolyzing the treated sugar cane bagasse obtained from stage c) with an enzyme, such that a cellulosic hydrolysate is produced; and
   e) fermenting the the cellulosic hydrolysate from stage d), such that a cellulosic ethanol is produced;
   wherein the at least one chemical agent added at stage c) is selected from the group consisting of ammonia, ammonium hydroxide, water steam, water, and combinations thereof, and
   wherein stages d) and e) are sequential or concurrent stages.

* * * * *